United States Patent
Pioszak

(10) Patent No.: US 10,464,983 B2
(45) Date of Patent: Nov. 5, 2019

(54) VARIANTS OF ADRENOMEDULLIN AND CALCITONIN GENE-RELATED PEPTIDE AND METHODS OF USE

(71) Applicant: The Board of Regents of the University of Oklahoma, Norman, OK (US)

(72) Inventor: Augen A. Pioszak, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/568,129

(22) PCT Filed: May 13, 2016

(86) PCT No.: PCT/US2016/032444
§ 371 (c)(1),
(2) Date: Oct. 20, 2017

(87) PCT Pub. No.: WO2016/183479
PCT Pub. Date: Nov. 17, 2016

(65) Prior Publication Data
US 2018/0141989 A1    May 24, 2018

Related U.S. Application Data

(60) Provisional application No. 62/160,899, filed on May 13, 2015.

(51) Int. Cl.
*A61K 38/00* (2006.01)
*C07K 14/585* (2006.01)
*C07K 14/575* (2006.01)

(52) U.S. Cl.
CPC .......... *C07K 14/585* (2013.01); *C07K 14/575* (2013.01); *C07K 14/57527* (2013.01); *A61K 38/00* (2013.01)

(58) Field of Classification Search
None
See application file for complete search history.

(56) References Cited

U.S. PATENT DOCUMENTS

| | | | | |
|---|---|---|---|---|
| 7,208,469 B2 * | 4/2007 | Reid | ............... | C07K 14/575 424/93.7 |
| 2011/0189205 A1 | 8/2011 | Dickerson et al. | | |
| 2013/0071410 A1 | 3/2013 | Boone et al. | | |
| 2014/0155329 A1 | 6/2014 | Hsu et al. | | |

FOREIGN PATENT DOCUMENTS

WO    2015017455 A1    2/2015

OTHER PUBLICATIONS

Kyani et al. Chem Biol Drug Des 2012; 79: 166-176.*
Barwell, et al.; "Mapping Interaction Sites Within the N-terminus of the Calcitonin Gene-Related Peptide Receptor; The Role of Residues 23-60 of the Calcitonin Receptor-Like Receptor," Elsevier Peptides (2010), vol. 31, pp. 170-176.
Booe, et al.; "Structural Basis for Receptor Activity-Modifying Protein-Dependent Selective Peptide Recognition by a G Protein-Coupled Receptor," Molecular Cell (2015), vol. 58, pp. 1-13.
Carpenter, et al.; "Turn Structures in CGRP C-Terminal Analogues Promote Stable Arrangements of Key Residue Side Chains," Biochemistry (2001), vol. 40, pp. 8317-8325.
Emsley, et al.; "Features and Development of Coot," Acta Crystallographica Section D Biological Crystallography (2010) vol. 66, pp. 486-501; doi:10.1107/S0907444910007493.
Hill, et al.; "Bacterial Expression and Purification of a Heterodimeric Adrenomedullin Receptor Extracellular Domain Complex Using DsbC-Assisted Disulfide Shuffling," Protein Expr Purif. (2013), vol. 88, No. 1, pp. 107-113.
Kusano, et al.; "Structural Basis for Extracellular Interactions Between Calcitonin Receptor-Like Receptor and Receptor Activity-Modifying Protein 2 for Adrenomedullin-Specific Binding," Protein Science (2012), vol. 21, pp. 199-210.
Lu, et al.; "OPUS-PSP: An Orientation-dependent Statistical All-atom Potential Derived from Side-Chain Packing," J. Mol. Biol. (2008), vol. 376, No. 1, pp. 288-301.
Mccoy, et al.,; "Phaser Crystallographic Software," Journal of Applied Crystallography (2007), vol. 40, pp. 658-674.
Moad, et al.; "Selective CGRP and Adrenomedullin Peptide Binding by Tethered RAMP-Calcitonin Receptor-like Receptor Extracellular Domain Fusion Proteins," Protein Science (2013), vol. 22, pp. 1775-1785.
Moore, et al.; "Mapping the CGRP Receptor Ligand Binding Domain: Tryptophan-84 of RAMP1 is Critical for Agonist and Antagonist Binding," Biochemical and Biophysical Research Communications (2010), vol. 394, pp. 141-145.
Murshudov, et al.; "Refinement of Macromolecular Structures by the Maximum-Likelihood Method," Acta Crystallographica Section D (1997), vol. 53, pp. 240-255.
Otwinowski, et al.; "Processing of X-Ray Diffraction Data Collected in Oscillation Mode in Methods in Enzymology," C.W.J. Carter, and R.M. Sweet, eds. New York: Academic Press (1997), pp. 307-326.
Pal, et al.; "Structural Basis for Hormone Recognition by the Human CRFR2α G Protein-coupled Receptor," The Journal of Biological Chemistry (2010), vol. 285, No. 51, pp. 40351-40361.
Parthier, et al.; "Crysal Structure of the Incretin-bound Extracellular Domain of a G Protein-coupled Receptor," PNAS (2007), vol. 104, No. 35, pp. 13942-13947.
Pioszak, et al.; "Molecular Recognition of Parathyroid Hormone by its G Protein-coupled Receptor," PNAS (2008), vol. 105, No. 13, pp. 5034-5039.

(Continued)

*Primary Examiner* — Jeanette M Lieb
(74) *Attorney, Agent, or Firm* — Dunlap Codding, P.C.

(57) ABSTRACT

Variant peptides of calcitonin gene-related peptide alpha (αCGRP), calcitonin gene-related peptide beta (βCGRP), and adrenomedullin (AM) are disclosed, wherein the variant peptides have high binding affinity and agonistic or antagonistic activity for at least one receptor complex of CLR:RAMP1, CLR:RAMP2, and CLR:RAMP3. Also disclosed are methods of use of the variant peptides in therapeutic treatments.

25 Claims, 19 Drawing Sheets
Specification includes a Sequence Listing.

(56) References Cited

OTHER PUBLICATIONS

Pronk, et al.,; "Gromacs 4.5: A High-Throughput and Highly Parallel Open Source Molecular Simulation Toolkit," Bioinformatics (2013), vol. 29, No. 7, pp. 845-854.
Rist, et al.; "From Micromolar to Nanomolar Affinity: A Systematic Approach to Identify the Binding Site of CGRP at the Human Calcitonin Gene-Related Peptide 1 Receptor," J. Med. Chem. (1998), vol. 41, pp. 117-123.
Rohl, et al.; "Protein Structure Prediction Using Rosetta," Methods in Enzymology (2004), vol. 383, pp. 66-93.
Sali, et al.; "Comparative Protein Modelling by Satisfaction of Spatial Restraints," J. Mol. Biol. (1993), vol. 234, pp. 779-815.
Ter Haar, et al.; "Crystal Structure of the Ectodomain Complex of the CGRP Receptor, a Class-B GPCR, Reveals the Site of Drug Antagonism," Structure (2010), vol. 18, pp. 1083-1093.
Underwood, et al.; "Crystal Structure of Glucagon-like Peptide-1 in Complex with the Extracellular Domain of the Glucagon-like Peptide-1 Receptor," The Joural of Biological Chemistry (2010), vol. 285, No. 1, pp. 723-730.
Watkins, et al.; Structure-activity Relationships for α-calcitonin Gene-related Peptide, British Journal of Pharmacology (2013), vol. 170, pp. 1308-1322.
Watkins, et al.; "Receptor Activity-modifying Protein-dependent Effects of Mutations in the Calcitonin Receptor-like Receptor: Implications for Adrenomedullin and Calcitonin Gene-related Peptide Pharmacology," British Journal of Pharmacology (2014), vol. 171, pp. 772-788.
Watkins, et al.; "Identification of Key Residues Involved in Adrenomedullin Binding to the AM1 Receptor," British Journal of Pharmacology (2013), vol. 169, pp. 143-155.
Winn, et al.; "Overview of the CCP4 Suite and Current Developments," Acta Crystallographica Section D Biological Crystallography (2011), vol. 67, pp. 235-242.
International Search Report, dated Oct. 21, 2016, in PCT/US2016/032444, filed May 13, 2016.
Written Opinion of the International Searching Authority, dated Oct. 21, 2016, in PCT/US2016/032444, filed May 13, 2016.

* cited by examiner

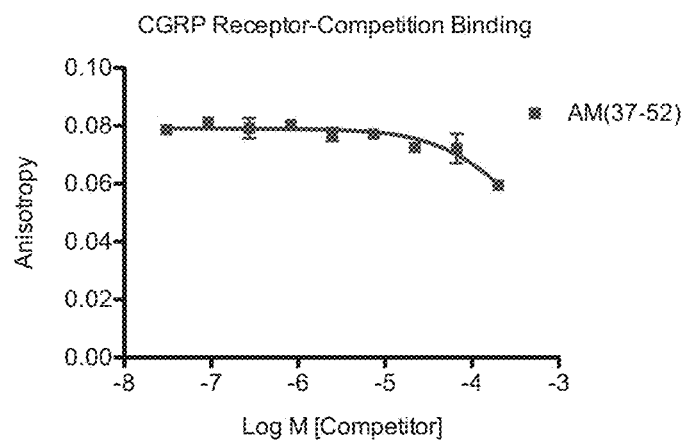
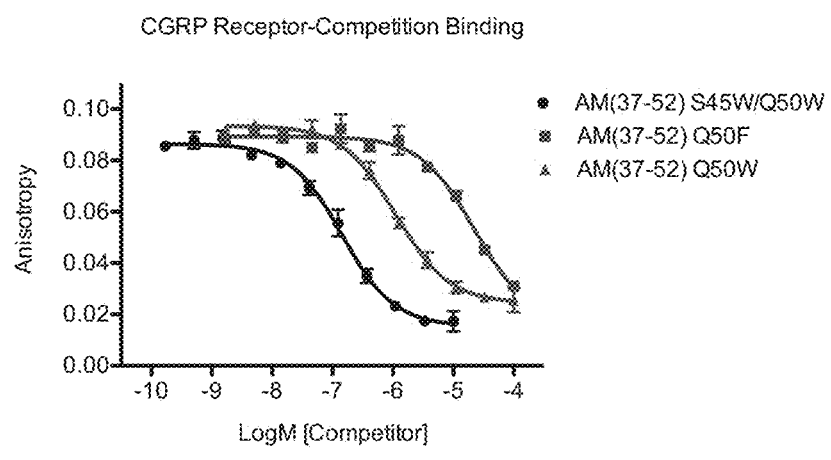
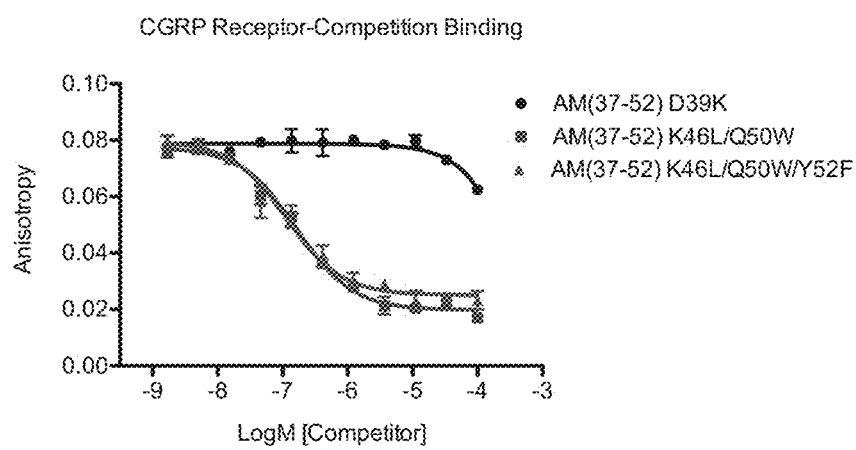
FIG. 2(A-C)

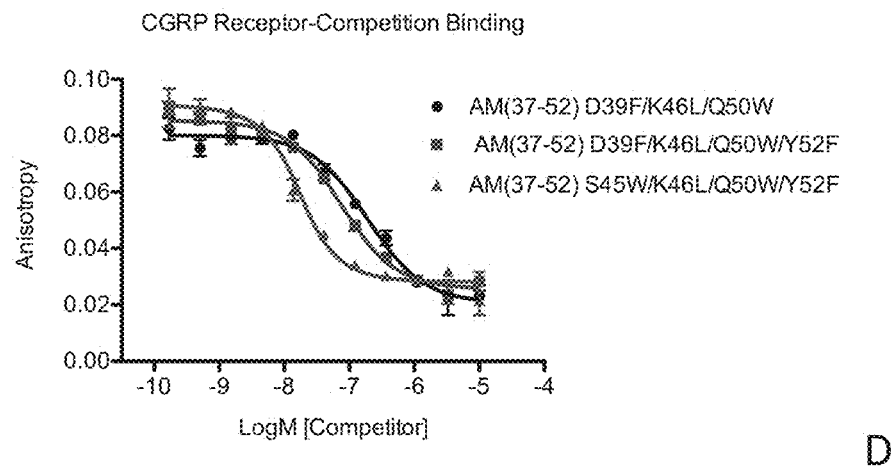
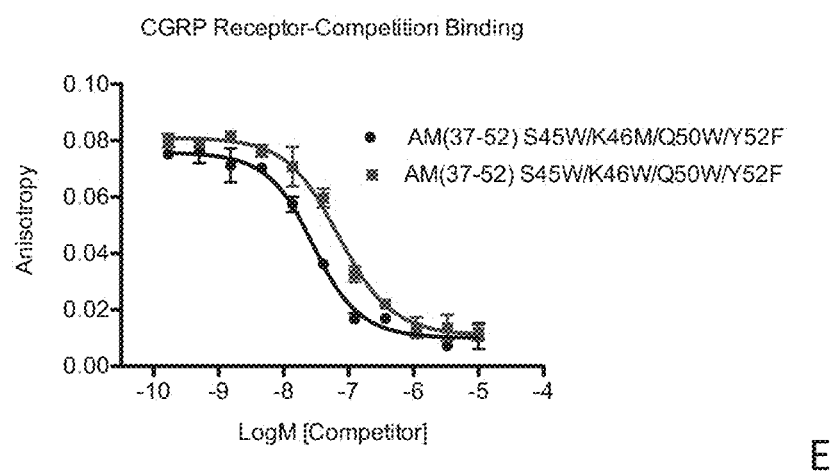
FIG. 2(D-E)

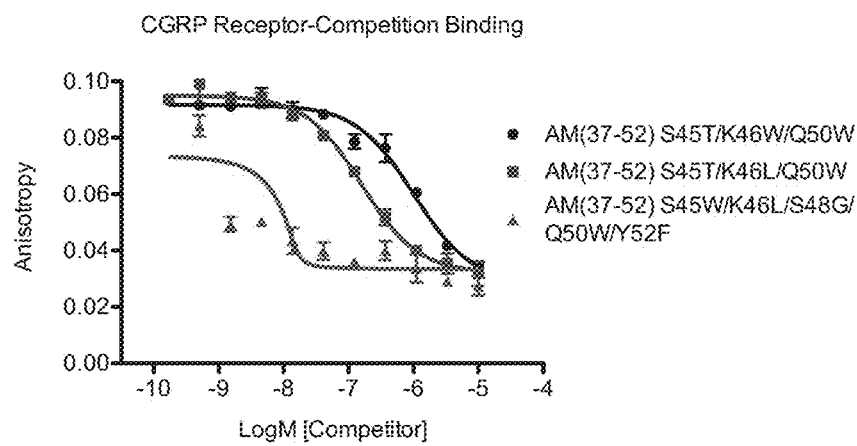
F
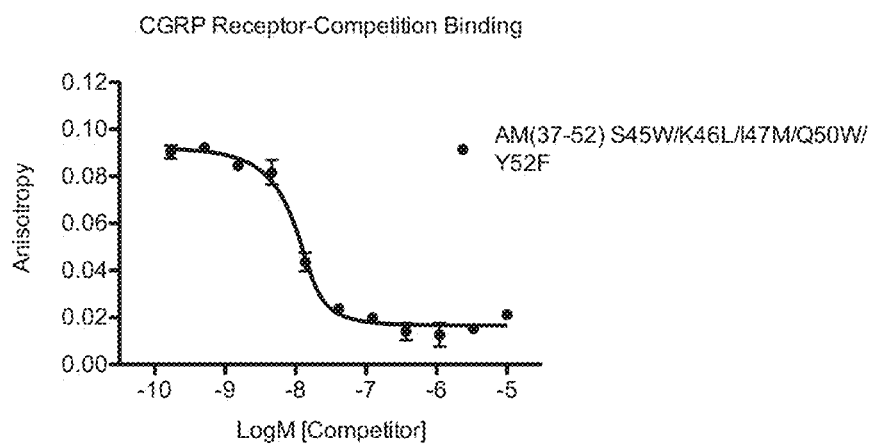
G
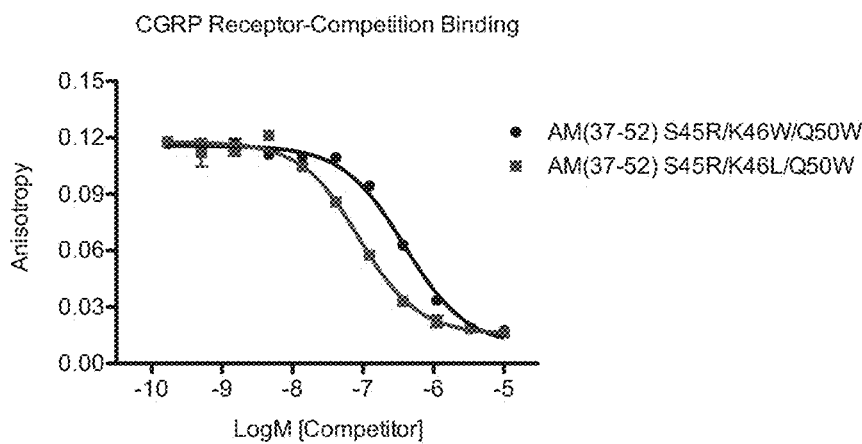
H
FIG. 2(F-H)

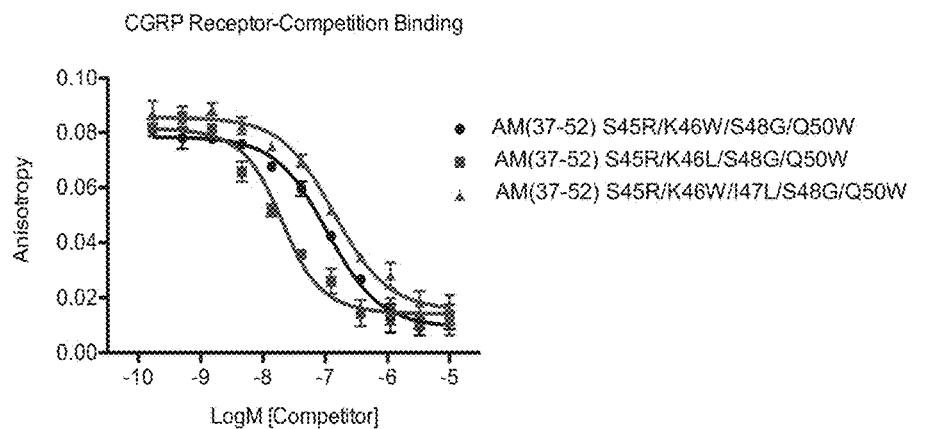
I
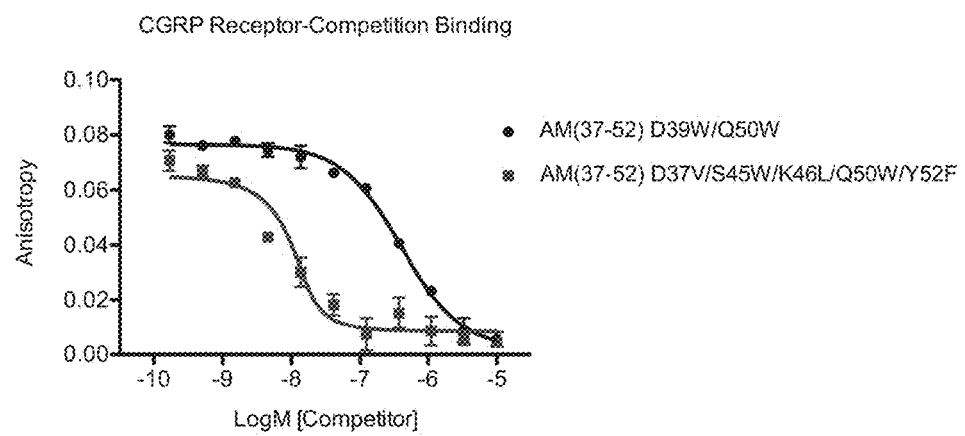
J
FIG. 2(I-J)

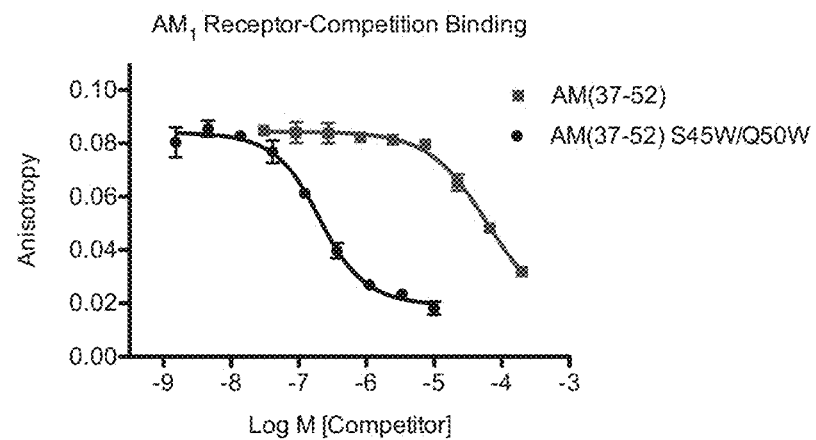
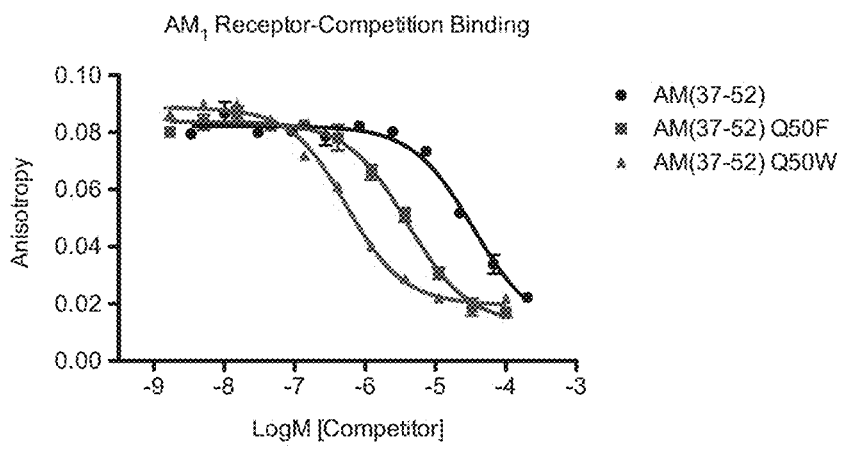
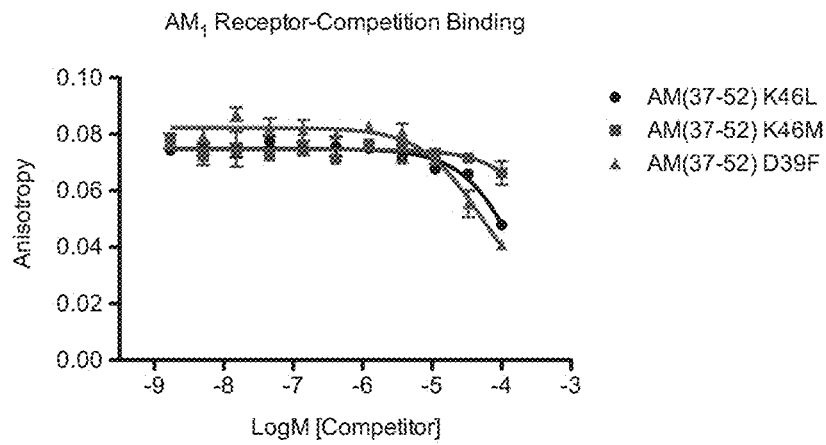
FIG. 3(A-C)

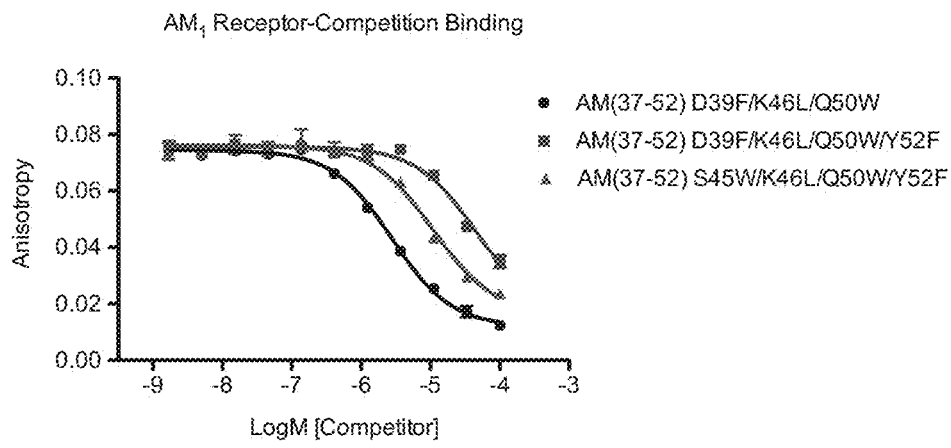
D
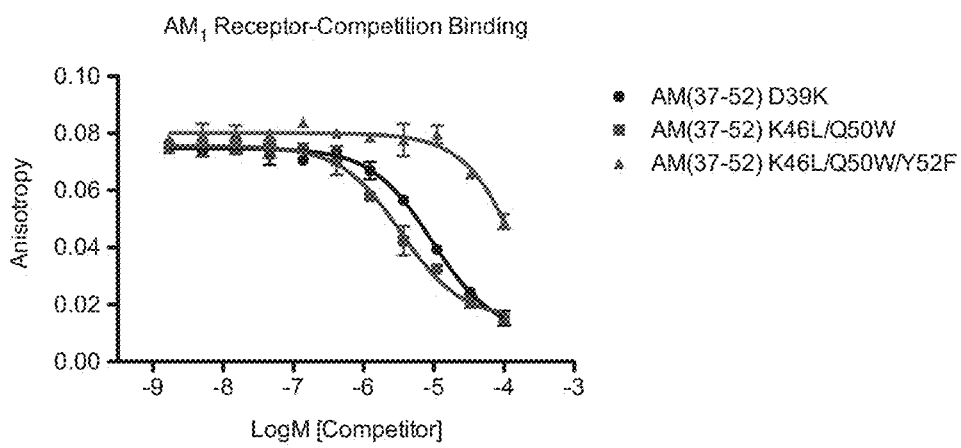
E
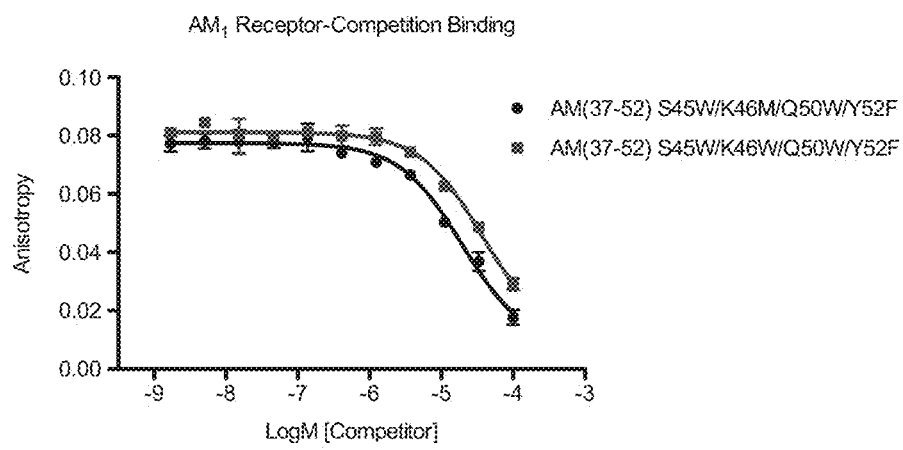
F
FIG. 3(D-F)

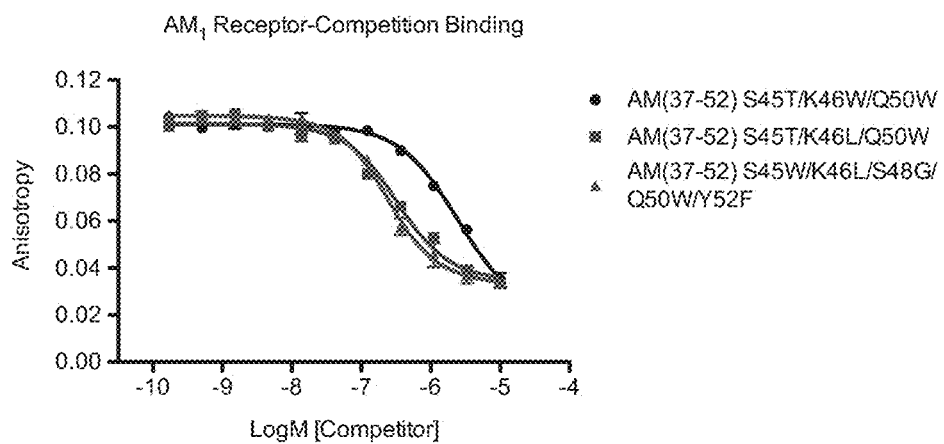
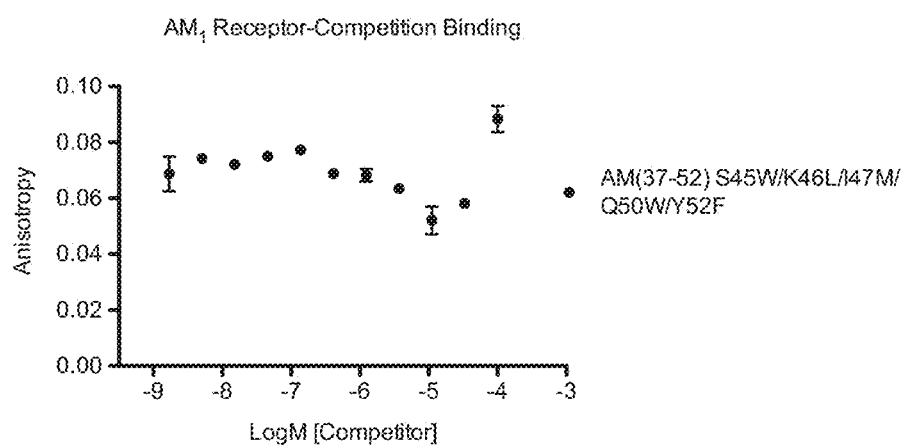
FIG. 3(G-H)

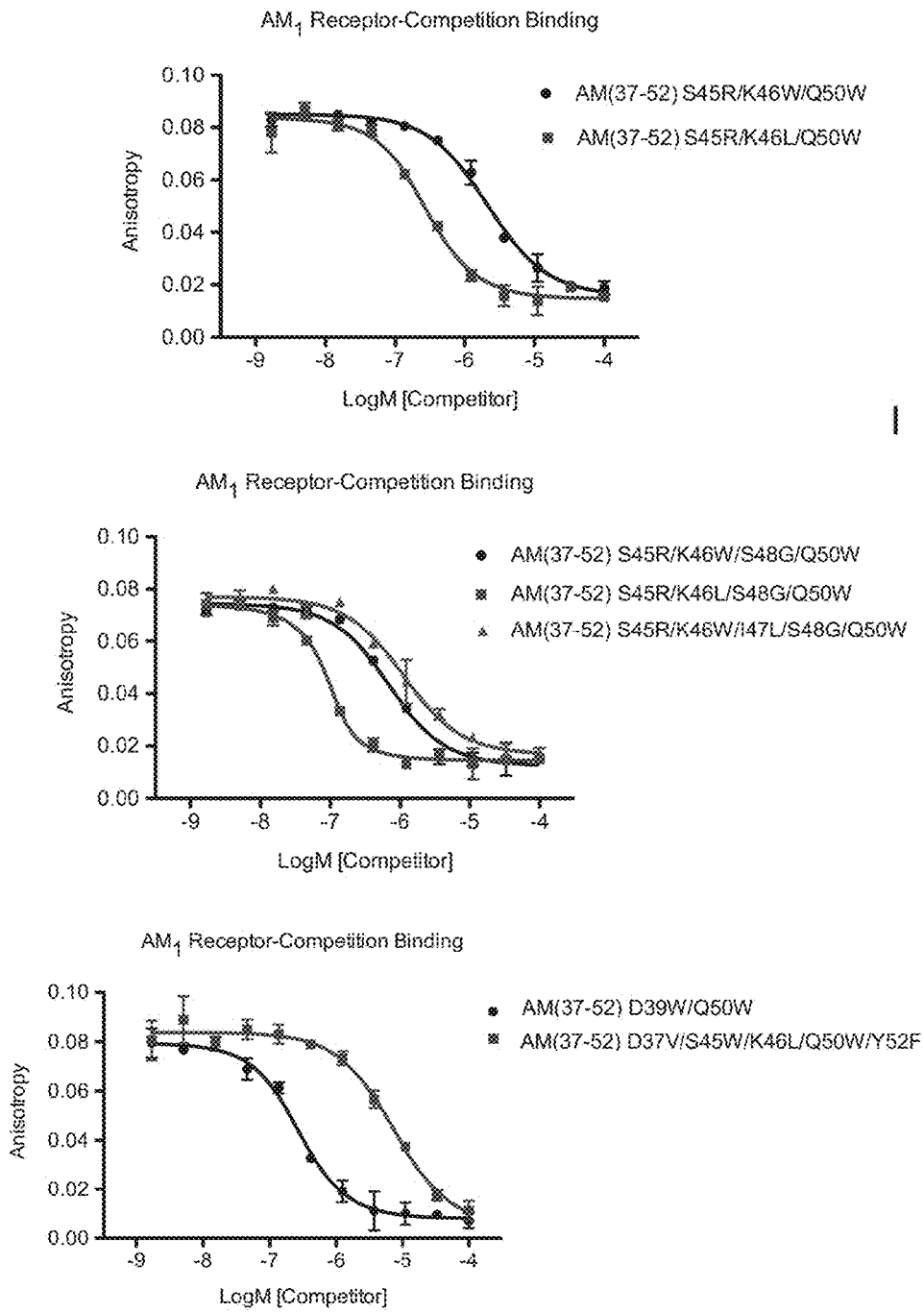
FIG. 3(I-K)

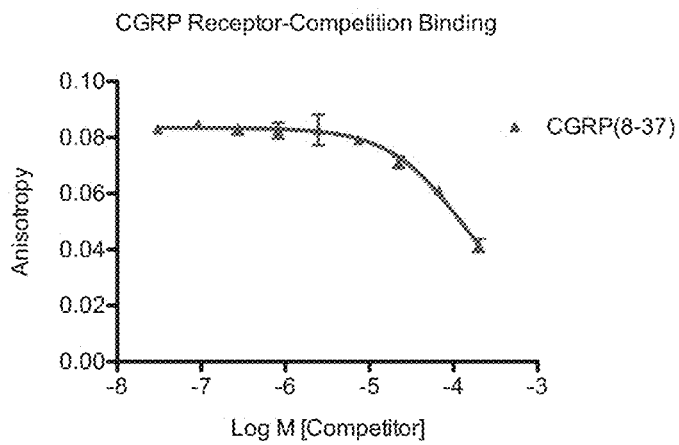
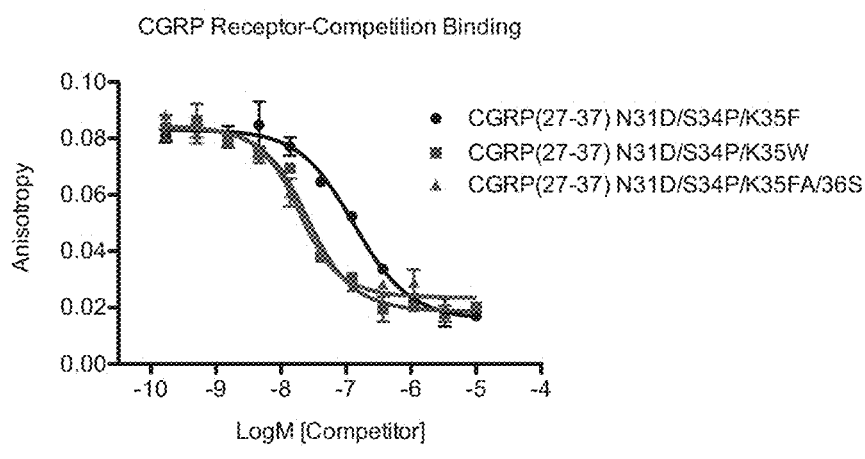
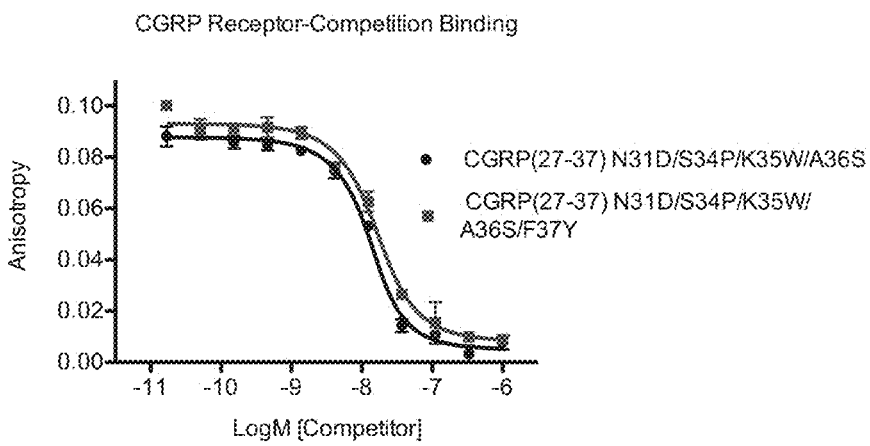
FIG. 4(A-C)

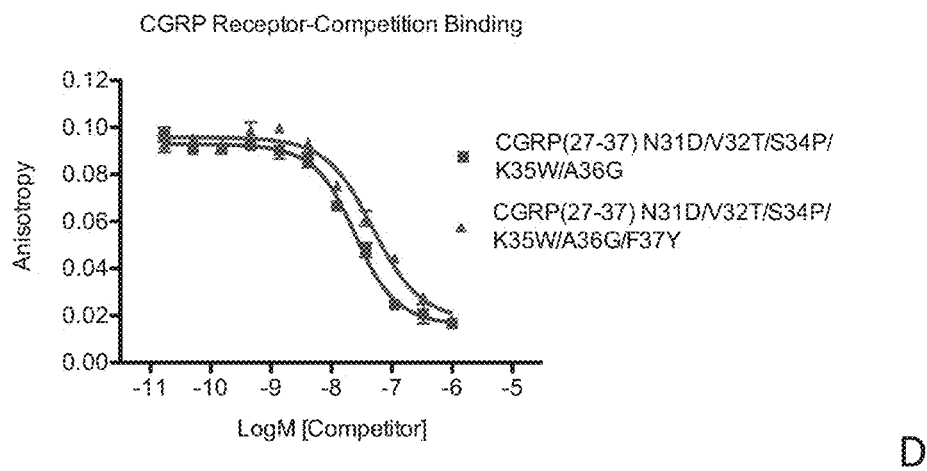
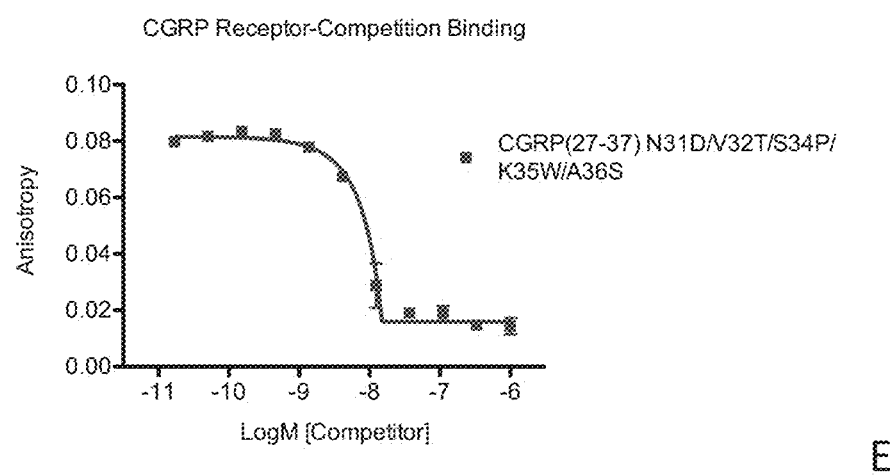
FIG. 4(D-E)

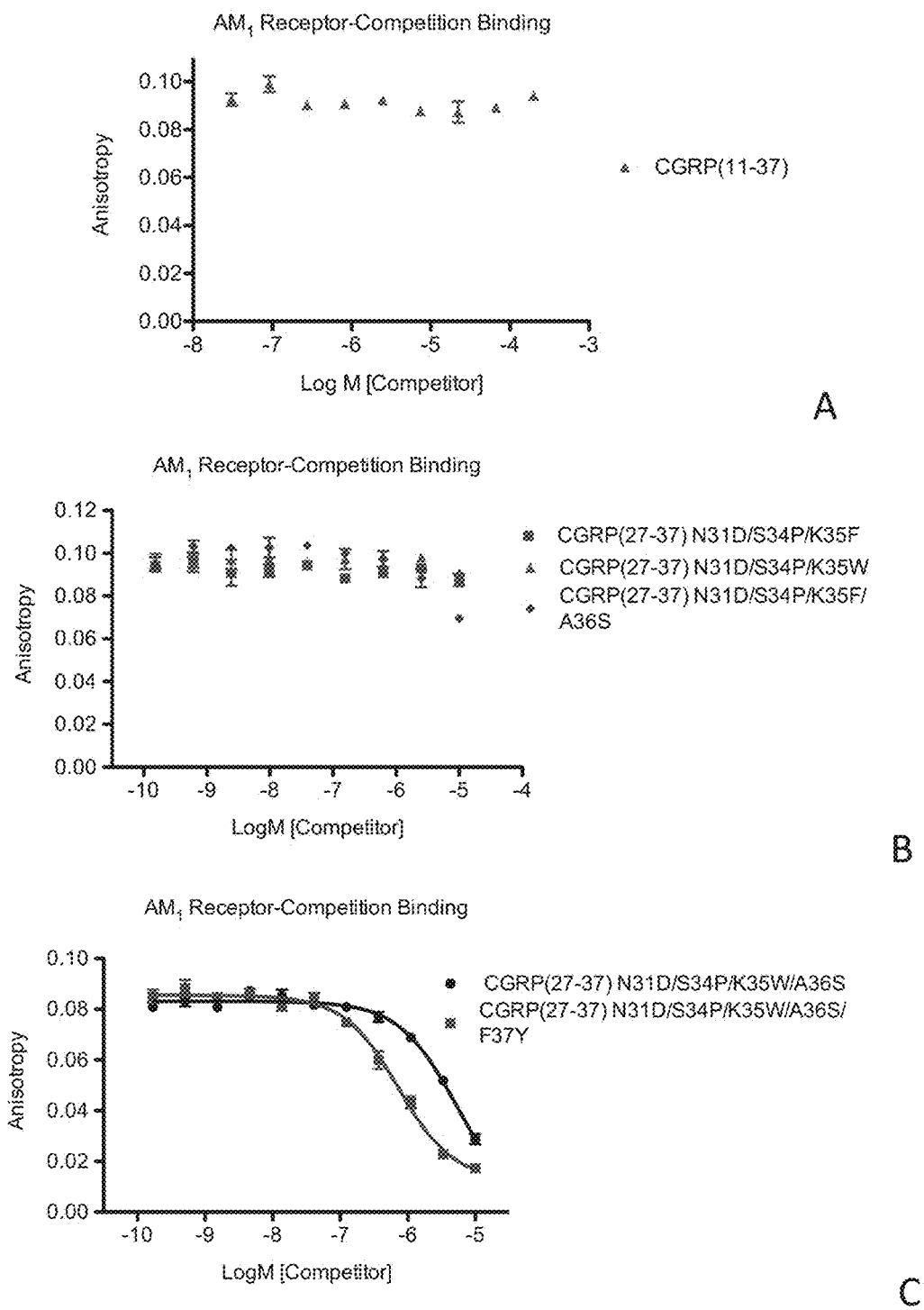
FIG. 5(A-C)

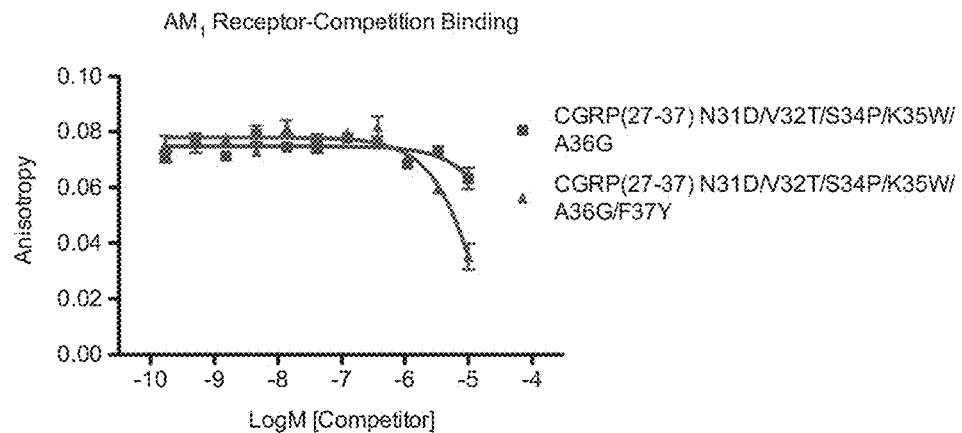
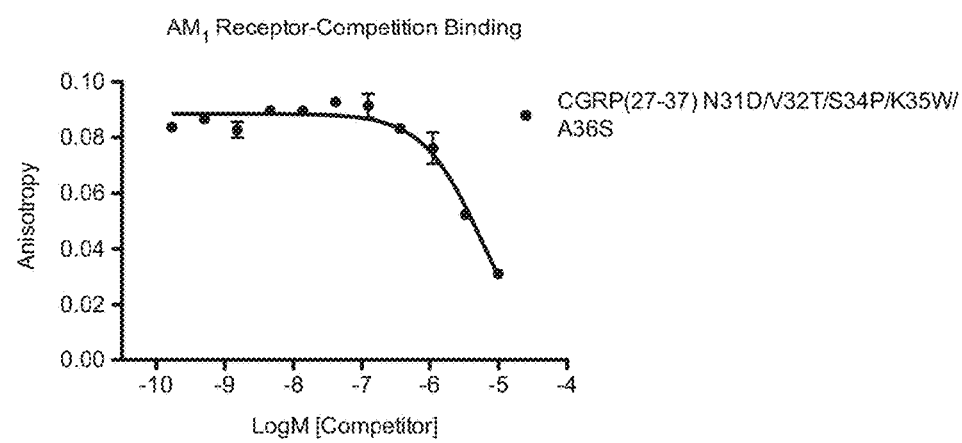
FIG. 5(D-E)

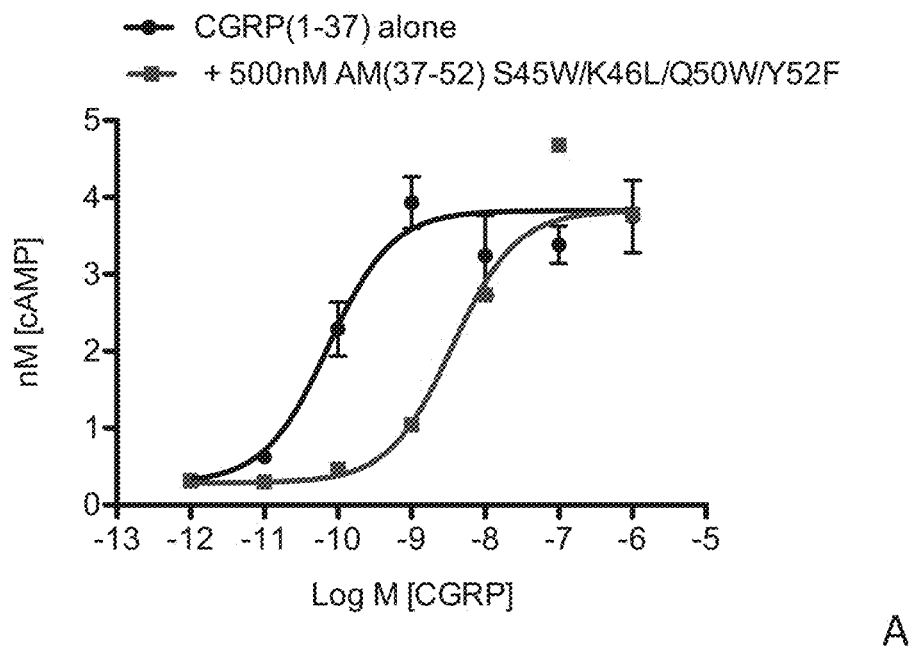
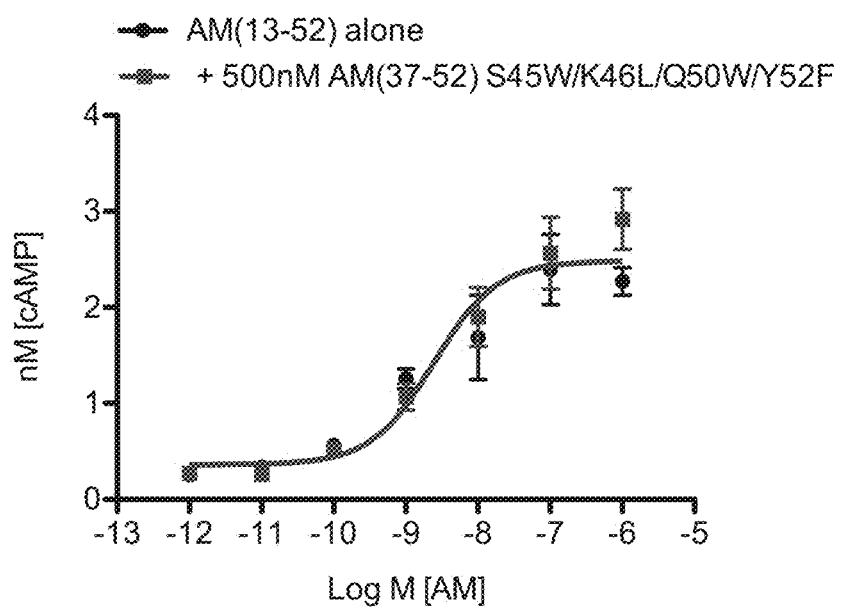
FIG. 7(A-B)

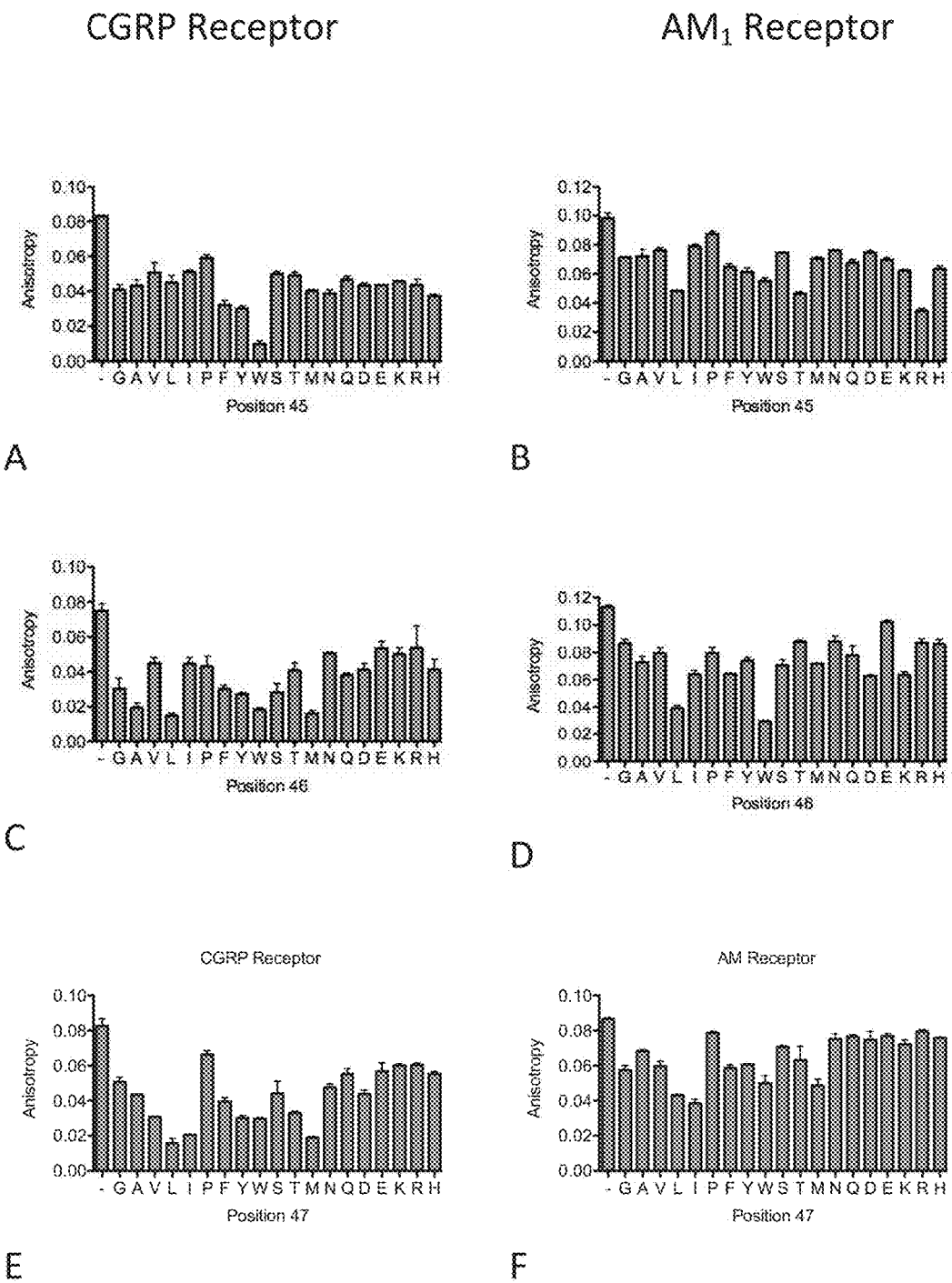
FIG. 8(A-F)

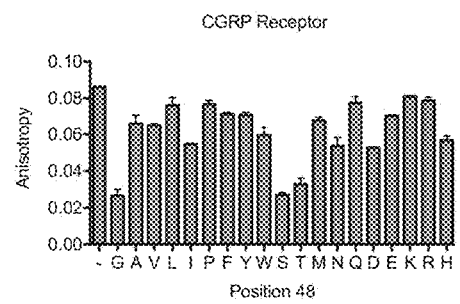
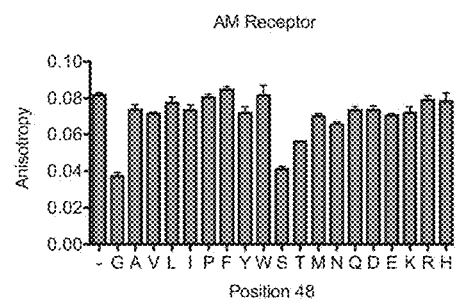
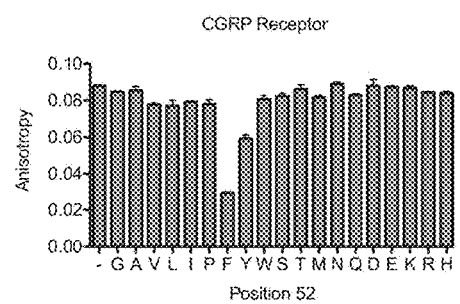
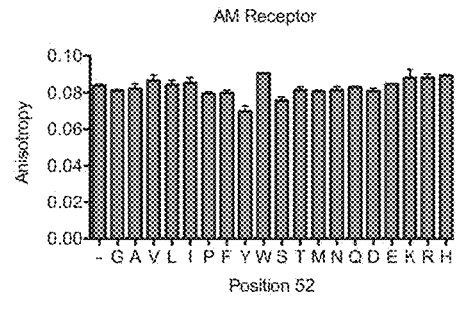
FIG. 8(G-J)

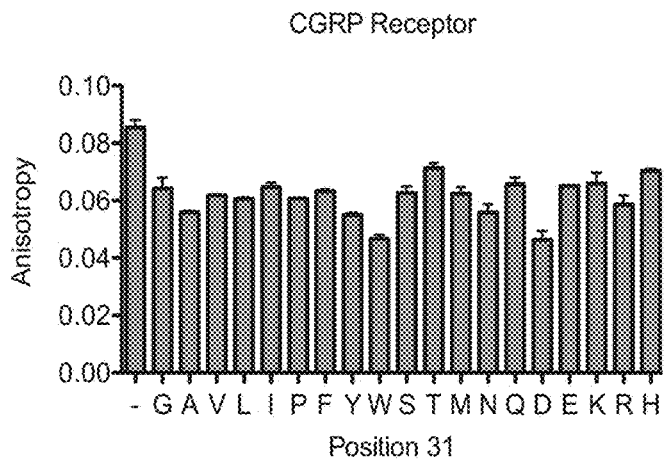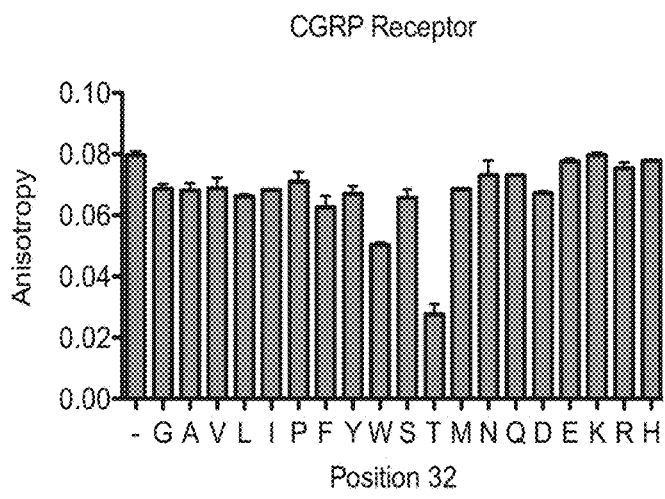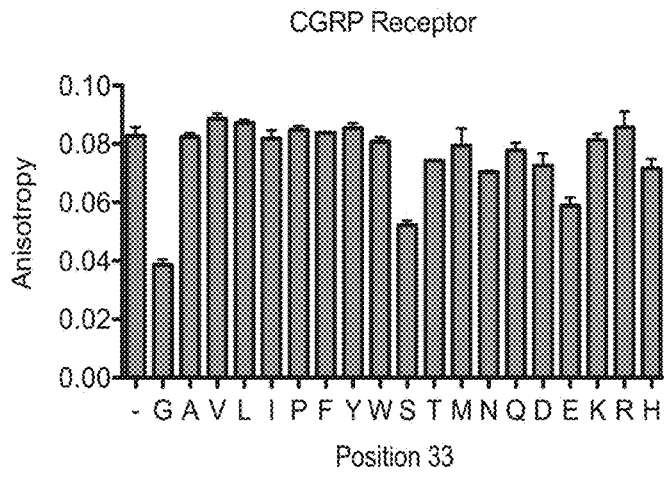
FIG. 9(A-C)

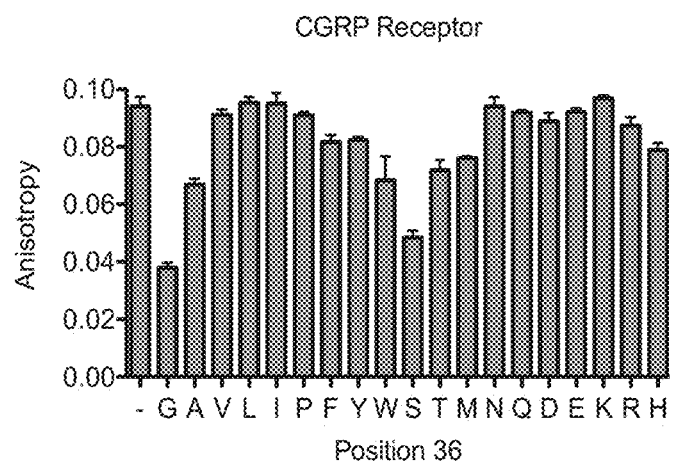
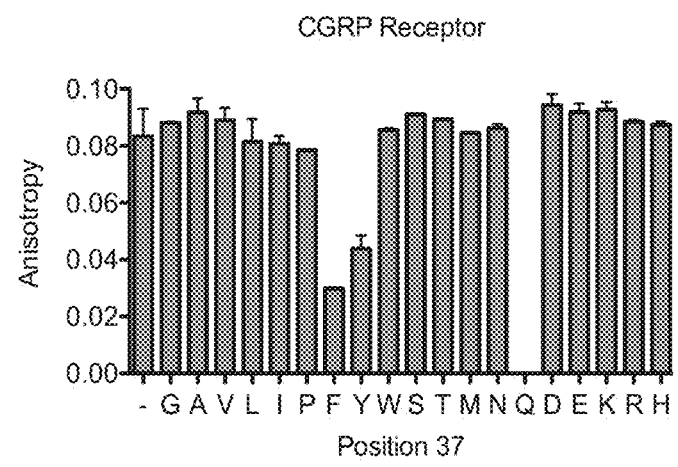
FIG. 9(D-E)

SEQUENCE LISTING

```
<160> NUMBER OF SEQ ID NOS: 54

<210> SEQ ID NO 1
<211> LENGTH: 52
<212> TYPE: PRT
<213> ORGANISM: Homo sapiens
<220> FEATURE:
<221> NAME/KEY: DISULFID
<222> LOCATION: (16)..(21)
<220> FEATURE:
<221> NAME/KEY: MOD_RES
<222> LOCATION: (52)..(52)
<223> OTHER INFORMATION: AMIDATION

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45

Pro Gln Gly Tyr
    50

<210> SEQ ID NO 2
<211> LENGTH: 40
<212> TYPE: PRT
<213> ORGANISM: Homo sapiens
<220> FEATURE:
<221> NAME/KEY: DISULFID
<222> LOCATION: (4)..(9)
<220> FEATURE:
<221> NAME/KEY: MOD_RES
<222> LOCATION: (40)..(40)
<223> OTHER INFORMATION: AMIDATION

<400> SEQUENCE: 2

Ser Phe Gly Cys Arg Phe Gly Thr Cys Thr Val Gln Lys Leu Ala His
1               5                   10                  15

Gln Ile Tyr Gln Phe Thr Asp Lys Asp Lys Asp Asn Val Ala Pro Arg
            20                  25                  30

Ser Lys Ile Ser Pro Gln Gly Tyr
        35                  40

<210> SEQ ID NO 3
<211> LENGTH: 31
<212> TYPE: PRT
```

```
<213> ORGANISM: Homo sapiens
<220> FEATURE:
<221> NAME/KEY: MOD_RES
<222> LOCATION: (31)..(31)
<223> OTHER INFORMATION: AMIDATION

<400> SEQUENCE: 3

Thr Val Gln Lys Leu Ala His Gln Ile Tyr Gln Phe Thr Asp Lys Asp
1               5                   10                  15

Lys Asp Asn Val Ala Pro Arg Ser Lys Ile Ser Pro Gln Gly Tyr
            20                  25                  30

<210> SEQ ID NO 4
<211> LENGTH: 16
<212> TYPE: PRT
<213> ORGANISM: Homo sapiens
<220> FEATURE:
<221> NAME/KEY: MOD_RES
<222> LOCATION: (16)..(16)
<223> OTHER INFORMATION: AMIDATION

<400> SEQUENCE: 4

Asp Lys Asp Asn Val Ala Pro Arg Ser Lys Ile Ser Pro Gln Gly Tyr
1               5                   10                  15

<210> SEQ ID NO 5
<211> LENGTH: 16
<212> TYPE: PRT
<213> ORGANISM: Artificial Sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 5

Asp Lys Asp Asn Val Ala Pro Arg Ser Lys Ile Ser Pro Phe Gly Tyr
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 6

Asp Lys Asp Asn Val Ala Pro Arg Ser Lys Ile Ser Pro Trp Gly Tyr
1               5                   10                  15

<210> SEQ ID NO 7
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 7

Asp Lys Asp Asn Val Ala Pro Arg Ser Leu Ile Ser Pro Gln Gly Tyr
1               5                   10                  15
```

<210> SEQ ID NO 8
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 8

Asp Lys Asp Asn Val Ala Pro Arg Ser Met Ile Ser Pro Gln Gly Tyr
 1               5                  10                  15

<210> SEQ ID NO 9
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 9

Asp Lys Asp Asn Val Ala Pro Arg Ser Trp Ile Ser Pro Gln Gly Tyr
 1               5                  10                  15

<210> SEQ ID NO 10
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 10

Asp Lys Lys Asn Val Ala Pro Arg Ser Lys Ile Ser Pro Gln Gly Tyr
 1               5                  10                  15

<210> SEQ ID NO 11
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 11

Asp Lys Asp Asn Val Ala Pro Arg Trp Lys Ile Ser Pro Trp Gly Tyr
 1               5                  10                  15

<210> SEQ ID NO 12
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)

<223> OTHER INFORMATION: AMIDATION

<400> SEQUENCE: 12

Asp Lys Asp Asn Val Ala Pro Arg Ser Leu Ile Ser Pro Trp Gly Tyr
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 13

Asp Lys Trp Asn Val Ala Pro Arg Ser Lys Ile Ser Pro Trp Gly Tyr
1               5                   10                  15

<210> SEQ ID NO 14
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 14

Asp Lys Lys Asn Val Ala Pro Arg Ser Lys Ile Ser Pro Phe Gly Tyr
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 15

Asp Lys Lys Asn Val Ala Pro Arg Ser Lys Ile Ser Pro Trp Gly Tyr
1               5                   10                  15

<210> SEQ ID NO 16
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 16

Asp Lys Asp Asn Val Ala Pro Arg Ser Leu Ile Ser Pro Trp Gly Phe
1               5                   10                  15

<210> SEQ ID NO 17
<211> LENGTH: 16
<212> TYPE: PRT

```
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 17

Asp Lys Phe Asn Val Ala Pro Arg Ser Leu Ile Ser Pro Trp Gly Tyr
1               5                   10                  15

<210> SEQ ID NO 18
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 18

Asp Lys Asp Asn Val Ala Pro Arg Arg Trp Ile Ser Pro Trp Gly Tyr
1               5                   10                  15

<210> SEQ ID NO 19
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 19

Asp Lys Asp Asn Val Ala Pro Arg Arg Leu Ile Ser Pro Trp Gly Tyr
1               5                   10                  15

<210> SEQ ID NO 20
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 20

Asp Lys Phe Asn Val Ala Pro Arg Ser Leu Ile Ser Pro Trp Gly Phe
1               5                   10                  15

<210> SEQ ID NO 21
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 21

Asp Lys Asp Asn Val Ala Pro Arg Trp Trp Ile Ser Pro Trp Gly Phe
```

```
<210> SEQ ID NO 22
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 22

Asp Lys Asp Asn Val Ala Pro Arg Trp Leu Ile Ser Pro Trp Gly Phe
1               5                   10                  15

<210> SEQ ID NO 23
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 23

Asp Lys Asp Asn Val Ala Pro Arg Trp Met Ile Ser Pro Trp Gly Phe
1               5                   10                  15

<210> SEQ ID NO 24
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 24

Asp Lys Asp Asn Val Ala Pro Arg Arg Trp Ile Gly Pro Trp Gly Tyr
1               5                   10                  15

<210> SEQ ID NO 25
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 25

Asp Lys Asp Asn Val Ala Pro Arg Arg Leu Ile Gly Pro Trp Gly Tyr
1               5                   10                  15

<210> SEQ ID NO 26
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
```

```
<222> LOCATION: (16)..(16)
<223> OTHER INFORMATION: AMIDATION

<400> SEQUENCE: 26

Val Lys Asp Asn Val Ala Pro Arg Trp Leu Ile Ser Pro Trp Gly Phe
1               5                   10                  15

<210> SEQ ID NO 27
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 27

Asp Lys Asp Asn Val Ala Pro Arg Trp Leu Ile Gly Pro Trp Gly Phe
1               5                   10                  15

<210> SEQ ID NO 28
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 28

Asp Lys Asp Asn Val Ala Pro Arg Trp Leu Met Ser Pro Trp Gly Phe
1               5                   10                  15

<210> SEQ ID NO 29
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 29

Asp Lys Asp Asn Val Ala Pro Arg Arg Trp Leu Gly Pro Trp Gly Tyr
1               5                   10                  15

<210> SEQ ID NO 30
<211> LENGTH: 16
<212> TYPE: PRT
<213> ORGANISM: Artificial sequence
<220> FEATURE:
<223> OTHER INFORMATION: Mutant of SEQ ID NO:4
<220> FEATURE:
<221> NAME/KEY: MOD_RES
<222> LOCATION: (16)..(16)
<223> OTHER INFORMATION: AMIDATION

<400> SEQUENCE: 30

Asp Lys Lys Asn Val Ala Pro Arg Arg Leu Ile Gly Pro Trp Gly Tyr
1               5                   10                  15

<210> SEQ ID NO 31
<211> LENGTH: 37
```

```
<212> TYPE: PRT
<213> ORGANISM: Homo sapiens
<220> FEATURE:
<221> NAME/KEY: DISULFID
<222> LOCATION: (2)..(7)
<220> FEATURE:
<221> NAME/KEY: MOD_RES
<222> LOCATION: (37)..(37)
<223> OTHER INFORMATION: AMIDATION

<400> SEQUENCE: 31

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 32
<211> LENGTH: 37
<212> TYPE: PRT
<213> ORGANISM: Homo sapiens
<220> FEATURE:
<221> NAME/KEY: DISULFID
<222> LOCATION: (2)..(7)
<220> FEATURE:
<221> NAME/KEY: MOD_RES
<222> LOCATION: (37)..(37)
<223> OTHER INFORMATION: AMIDATION

<400> SEQUENCE: 32

Ala Cys Asn Thr Ala Thr Cys Val Thr His Arg Leu Ala Gly Leu Leu
1               5                   10                  15

Ser Arg Ser Gly Gly Met Val Lys Ser Asn Phe Val Pro Thr Asn Val
            20                  25                  30

Gly Ser Lys Ala Phe
        35

<210> SEQ ID NO 33
<211> LENGTH: 30
<212> TYPE: PRT
<213> ORGANISM: Homo sapiens
<220> FEATURE:
<221> NAME/KEY: MOD_RES
<222> LOCATION: (30)..(30)
<223> OTHER INFORMATION: AMIDATION

<400> SEQUENCE: 33

Val Thr His Arg Leu Ala Gly Leu Leu Ser Arg Ser Gly Gly Val Val
1               5                   10                  15

Lys Asn Asn Phe Val Pro Thr Asn Val Gly Ser Lys Ala Phe
            20                  25                  30

<210> SEQ ID NO 34
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 34

Phe Val Pro Thr Asn Val Gly Ser Lys Ala Phe
1               5                   10
```

```
<210> SEQ ID NO 35
<211> LENGTH: 11
<212> TYPE: PRT
<213> ORGANISM: Homo sapiens
<220> FEATURE:
<221> NAME/KEY: MOD_RES
<222> LOCATION: (11)..(11)
<223> OTHER INFORMATION: AMIDATION

<400> SEQUENCE: 35

Phe Val Pro Thr Asp Val Gly Pro Phe Ala Phe
1               5                   10

<210> SEQ ID NO 36
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 36

Phe Val Pro Thr Asp Val Gly Pro Trp Ala Phe
1               5                   10

<210> SEQ ID NO 37
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 37

Phe Val Pro Thr Asp Val Gly Pro Trp Ala Tyr
1               5                   10

<210> SEQ ID NO 38
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 38

Phe Val Pro Thr Asp Val Gly Pro Phe Ser Phe
1               5                   10

<210> SEQ ID NO 39
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 39
```

```
Phe Val Pro Thr Asp Val Gly Pro Trp Ser Phe
1               5                   10

<210> SEQ ID NO 40
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 40

Phe Val Pro Thr Asp Val Gly Pro Trp Ser Tyr
1               5                   10

<210> SEQ ID NO 41
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 41

Phe Val Pro Thr Asp Thr Gly Pro Trp Gly Phe
1               5                   10

<210> SEQ ID NO 42
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 42

Phe Val Pro Thr Asp Thr Gly Pro Trp Ser Phe
1               5                   10

<210> SEQ ID NO 43
<211> LENGTH: 11
<212> TYPE: PRT
<213> ORGANISM: Artificial sequence
<220> FEATURE:
<223> OTHER INFORMATION: Mutant of SEQ ID NO:34
<220> FEATURE:
<221> NAME/KEY: MOD_RES
<222> LOCATION: (11)..(11)
<223> OTHER INFORMATION: AMIDATION

<400> SEQUENCE: 43

Phe Val Pro Thr Asp Thr Gly Pro Trp Gly Tyr
1               5                   10

<210> SEQ ID NO 44
<211> LENGTH: 8
<212> TYPE: PRT
<213> ORGANISM: Artificial sequence
<220> FEATURE:
<223> OTHER INFORMATION: Mutant of amino acids 30-37 of SEQ ID NO:31
<220> FEATURE:
```

```
<221> NAME/KEY: MOD_RES
<222> LOCATION: (8)..(8)
<223> OTHER INFORMATION: AMIDATION

<400> SEQUENCE: 44

Thr Asp Val Gly Pro Trp Ala Phe
1               5

<210> SEQ ID NO 45
<211> LENGTH: 8
<212> TYPE: PRT
<213> ORGANISM: Artificial sequence
<220> FEATURE:
<223> OTHER INFORMATION: Mutant of amino acids 30-37 of SEQ ID NO:31
<220> FEATURE:
<221> NAME/KEY: MOD_RES
<222> LOCATION: (8)..(8)
<223> OTHER INFORMATION: AMIDATION

<400> SEQUENCE: 45

Thr Asp Val Gly Pro Trp Ser Phe
1               5

<210> SEQ ID NO 46
<211> LENGTH: 8
<212> TYPE: PRT
<213> ORGANISM: Artificial sequence
<220> FEATURE:
<223> OTHER INFORMATION: Mutant of amino acids 30-37 of SEQ ID NO:31
<220> FEATURE:
<221> NAME/KEY: MOD_RES
<222> LOCATION: (8)..(8)
<223> OTHER INFORMATION: AMIDATION

<400> SEQUENCE: 46

Thr Asp Val Gly Pro Trp Ser Tyr
1               5

<210> SEQ ID NO 47
<211> LENGTH: 40
<212> TYPE: PRT
<213> ORGANISM: Homo sapiens
<220> FEATURE:
<221> NAME/KEY: DISULFID
<222> LOCATION: (3)..(8)
<220> FEATURE:
<221> NAME/KEY: MOD_RES
<222> LOCATION: (40)..(40)
<223> OTHER INFORMATION: AMIDATION

<400> SEQUENCE: 47

Val Gly Cys Val Leu Gly Thr Cys Gln Val Gln Asn Leu Ser His Arg
1               5                   10                  15

Leu Trp Gln Leu Met Gly Pro Ala Gly Arg Gln Asp Ser Ala Pro Val
            20                  25                  30

Asp Pro Ser Ser Pro His Ser Tyr
            35                  40

<210> SEQ ID NO 48
<211> LENGTH: 24
<212> TYPE: PRT
<213> ORGANISM: Homo sapiens

<400> SEQUENCE: 48

Val Gly Cys Val Leu Gly Thr Cys Gln Val Gln Asn Leu Ser His Arg
1               5                   10                  15

Leu Trp Gln Leu Met Gly Pro Ala
```

20

<210> SEQ ID NO 49
<211> LENGTH: 16
<212> TYPE: PRT
<213> ORGANISM: Artificial sequence
<220> FEATURE:
<223> OTHER INFORMATION: Variants based on amino acids 37-52 of SEQ ID
      NO:1
<220> FEATURE:
<221> NAME/KEY: MISC_FEATURE
<222> LOCATION: (1)..(1)
<223> OTHER INFORMATION: X is A, D, V, L or I
<220> FEATURE:
<221> NAME/KEY: MISC_FEATURE
<222> LOCATION: (3)..(3)
<223> OTHER INFORMATION: X is D, F, M, Y, V, I, E, K, W, L, or R
<220> FEATURE:
<221> NAME/KEY: MISC_FEATURE
<222> LOCATION: (9)..(9)
<223> OTHER INFORMATION: X is S, W, Y, F, R, T, or L
<220> FEATURE:
<221> NAME/KEY: MISC_FEATURE
<222> LOCATION: (10)..(10)
<223> OTHER INFORMATION: X is K, G, L, M, Y, A, W, or F
<220> FEATURE:
<221> NAME/KEY: MISC_FEATURE
<222> LOCATION: (11)..(11)
<223> OTHER INFORMATION: X is I, L, or M
<220> FEATURE:
<221> NAME/KEY: MISC_FEATURE
<222> LOCATION: (12)..(12)
<223> OTHER INFORMATION: X is S, T, or G
<220> FEATURE:
<221> NAME/KEY: MISC_FEATURE
<222> LOCATION: (14)..(14)
<223> OTHER INFORMATION: X is Q, F, Y, W, or H
<220> FEATURE:
<221> NAME/KEY: MISC_FEATURE
<222> LOCATION: (16)..(16)
<223> OTHER INFORMATION: X is Y or F.
<220> FEATURE:
<221> NAME/KEY: MOD_RES
<222> LOCATION: (16)..(16)
<223> OTHER INFORMATION: AMIDATION

<400> SEQUENCE: 49

Xaa Lys Xaa Asn Val Ala Pro Arg Xaa Xaa Xaa Xaa Pro Xaa Gly Xaa
1               5                   10                  15

<210> SEQ ID NO 50
<211> LENGTH: 11
<212> TYPE: PRT
<213> ORGANISM: Artificial sequence
<220> FEATURE:
<223> OTHER INFORMATION: Variants based on amino acids 42-52 of SEQ ID
      NO:1
<220> FEATURE:
<221> NAME/KEY: MISC_FEATURE
<222> LOCATION: (4)..(4)
<223> OTHER INFORMATION: X is S, W, Y, F, R, T, or L
<220> FEATURE:
<221> NAME/KEY: MISC_FEATURE
<222> LOCATION: (5)..(5)
<223> OTHER INFORMATION: X is K, G, L, M, Y, A, W, or F
<220> FEATURE:
<221> NAME/KEY: MISC_FEATURE
<222> LOCATION: (6)..(6)
<223> OTHER INFORMATION: X is I, L, or M
<220> FEATURE:
<221> NAME/KEY: MISC_FEATURE
<222> LOCATION: (7)..(7)
<223> OTHER INFORMATION: X is S, T, or G
<220> FEATURE:
<221> NAME/KEY: MISC_FEATURE
<222> LOCATION: (9)..(9)

```
<223> OTHER INFORMATION: X is Q, F, Y, W, or H
<220> FEATURE:
<221> NAME/KEY: MISC_FEATURE
<222> LOCATION: (11)..(11)
<223> OTHER INFORMATION: X is Y or F
<220> FEATURE:
<221> NAME/KEY: MOD_RES
<222> LOCATION: (11)..(11)
<223> OTHER INFORMATION: AMIDATION

<400> SEQUENCE: 50

Ala Pro Arg Xaa Xaa Xaa Xaa Pro Xaa Gly Xaa
1               5                   10

<210> SEQ ID NO 51
<211> LENGTH: 11
<212> TYPE: PRT
<213> ORGANISM: Artificial sequence
<220> FEATURE:
<223> OTHER INFORMATION: Variants based on amino acids 27-37 of SEQ ID
      NO:31
<220> FEATURE:
<221> NAME/KEY: MISC_FEATURE
<222> LOCATION: (5)..(5)
<223> OTHER INFORMATION: X is N, D, or W
<220> FEATURE:
<221> NAME/KEY: MISC_FEATURE
<222> LOCATION: (6)..(6)
<223> OTHER INFORMATION: X is V, T, or W
<220> FEATURE:
<221> NAME/KEY: MISC_FEATURE
<222> LOCATION: (8)..(8)
<223> OTHER INFORMATION: X is P or S
<220> FEATURE:
<221> NAME/KEY: MISC_FEATURE
<222> LOCATION: (9)..(9)
<223> OTHER INFORMATION: X is W, Y, or H
<220> FEATURE:
<221> NAME/KEY: MISC_FEATURE
<222> LOCATION: (10)..(10)
<223> OTHER INFORMATION: X is A, S, or G
<220> FEATURE:
<221> NAME/KEY: MISC_FEATURE
<222> LOCATION: (11)..(11)
<223> OTHER INFORMATION: X is Y or F
<220> FEATURE:
<221> NAME/KEY: MOD_RES
<222> LOCATION: (11)..(11)
<223> OTHER INFORMATION: AMIDATION

<400> SEQUENCE: 51

Phe Val Pro Thr Xaa Xaa Gly Xaa Xaa Xaa Xaa
1               5                   10

<210> SEQ ID NO 52
<211> LENGTH: 8
<212> TYPE: PRT
<213> ORGANISM: Artificial sequence
<220> FEATURE:
<223> OTHER INFORMATION: Variants based on amino acids 30-37 of SEQ ID
      NO:31
<220> FEATURE:
<221> NAME/KEY: MISC_FEATURE
<222> LOCATION: (2)..(2)
<223> OTHER INFORMATION: X is N, D, or W
<220> FEATURE:
<221> NAME/KEY: MISC_FEATURE
<222> LOCATION: (3)..(3)
<223> OTHER INFORMATION: X is V, T, or W
<220> FEATURE:
<221> NAME/KEY: MISC_FEATURE
<222> LOCATION: (5)..(5)
<223> OTHER INFORMATION: X is P or S
<220> FEATURE:
<221> NAME/KEY: MISC_FEATURE
```

```
<222> LOCATION: (6)..(6)
<223> OTHER INFORMATION: X is W, Y, or H
<220> FEATURE:
<221> NAME/KEY: MISC_FEATURE
<222> LOCATION: (7)..(7)
<223> OTHER INFORMATION: X is A, S, or G
<220> FEATURE:
<221> NAME/KEY: MISC_FEATURE
<222> LOCATION: (8)..(8)
<223> OTHER INFORMATION: X is F or Y
<220> FEATURE:
<221> NAME/KEY: MOD_RES
<222> LOCATION: (8)..(8)
<223> OTHER INFORMATION: AMIDATION

<400> SEQUENCE: 52

Thr Xaa Xaa Gly Xaa Xaa Xaa Xaa
1               5

<210> SEQ ID NO 53
<211> LENGTH: 16
<212> TYPE: PRT
<213> ORGANISM: Artificial sequence
<220> FEATURE:
<223> OTHER INFORMATION: Amino acid sequence used to create variant
      peptide positional libraries based on amino acids 37-52 of SEQ ID
      NO:1
<220> FEATURE:
<221> NAME/KEY: MISC_FEATURE
<222> LOCATION: (9)..(9)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (10)..(10)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (11)..(11)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (12)..(12)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (16)..(16)
<223> OTHER INFORMATION: X is A, R, N, D, E, Q, G, H, I, L, K, M, F, P,
      S, T, W, Y, or V
<220> FEATURE:
<221> NAME/KEY: MOD_RES
<222> LOCATION: (16)..(16)
<223> OTHER INFORMATION: AMIDATION

<400> SEQUENCE: 53

Asp Lys Asp Asn Val Ala Pro Arg Xaa Xaa Xaa Xaa Pro Trp Gly Xaa
1               5                   10                  15

<210> SEQ ID NO 54
<211> LENGTH: 11
<212> TYPE: PRT
<213> ORGANISM: Artificial sequence
<220> FEATURE:
<223> OTHER INFORMATION: Amino acid sequence used to create variant
      peptide positional libraries based on amino acids 27-37 of SEQ ID
      NO:31
<220> FEATURE:
<221> NAME/KEY: MISC_FEATURE
<222> LOCATION: (5)..(5)
<223> OTHER INFORMATION: X is A, R, N, D, E, Q, G, H, I, L, K, M, F, P,
      S, T, W, Y, or V
<220> FEATURE:
```

```
<221> NAME/KEY: MISC_FEATURE
<222> LOCATION: (6)..(6)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (7)..(7)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (10)..(10)
<223> OTHER INFORMATION: X is A, R, N, D, E, Q, G, H, I, L, K, M, F, P,
      S, T, W, Y, or V
<220> FEATURE:
<221> NAME/KEY: MISC_FEATURE
<222> LOCATION: (11)..(11)
<223> OTHER INFORMATION: X is A, R, N, D, E, Q, G, H, I, L, K, M, F, P,
      S, T, W, Y, or V
<220> FEATURE:
<221> NAME/KEY: MOD_RES
<222> LOCATION: (11)..(11)
<223> OTHER INFORMATION: AMIDATION

<400> SEQUENCE: 54

Phe Val Pro Thr Xaa Xaa Xaa Pro Trp Xaa Xaa
1               5                   10
```

US 10,464,983 B2

VARIANTS OF ADRENOMEDULLIN AND CALCITONIN GENE-RELATED PEPTIDE AND METHODS OF USE

CROSS REFERENCE TO RELATED APPLICATIONS/INCORPORATION BY REFERENCE STATEMENT

This application is a US national stage application filed under 35 USC § 371 of International Application No. PCT/US2016/032444, filed May 13, 2016; which claims benefit under 35 USC § 119(e) of Provisional Application U.S. Ser. No. 62/160,899, filed May 13, 2015. The entire contents of each of the above-referenced applications are hereby expressly incorporated herein by reference.

STATEMENT REGARDING FEDERALLY SPONSORED RESEARCH OR DEVELOPMENT

This invention was made with government support from National Institutes of Health (NIH) grant R01GM104251. The government has certain rights in the invention.

BACKGROUND

G protein-coupled receptors (GPCRs) are a large family of cell surface receptors that regulate a multitude of biological processes in response to a diverse array of stimuli, and they are important drug targets. The class B/Secretin family of GPCRs in humans includes fifteen receptors that are activated by diverse neuropeptides, peptide paracrine factors and peptide endocrine hormones. Class B GPCRs comprise an extracellular domain (ECD) of about 120 amino acids in addition to a 7-transmembrane (7TM) domain in the membrane. The ECD has an N-terminal α-helix and a set of β-sheets held together by three disulfide bonds. Activating peptides bind class B GPCRs via a "two-domain" model, whereby the C-terminal region of the peptide binds the ECD, and the N-terminal region of the peptide binds and activates the 7TM domain. Certain of the activating peptides bind as extended α-helices to the same region of the receptor, in a groove between the N- and C-termini of the isolated ECDs. However, the mechanism of binding of the calcitonin (CT) family of this group of Class B GPCR-activating peptides has been unknown.

Members of the CT family of activating peptides include, for example, calcitonin gene-related peptide alpha (αCGRP), calcitonin gene-related peptide beta (βCGRP), adrenomedullin (AM), adrenomedullin 2/intermedin (AM2), amylin (Amy), and CT. These C-terminally amidated peptides have a range of actions including neurogenic inflammation, e.g., as a factor in migraine headache pathogenesis (CGRP), vasodilation/cardioprotection (CGRP, AM and AM2), and regulation of blood and lymphatic vascular development (AM), nutrient intake and blood glucose (Amy), and bone turnover (CT). CGRP in the trigeminovascular system acts as a pain signaling neurotransmitter. Elevated CGRP levels are associated with migraines, and exogenous administration of CGRP to migraineurs triggers migraines. Small molecule antagonists of the CGRP receptor that bind the ECD complex showed efficacy in clinical trials, but were abandoned because of toxicity unrelated to CGRP signaling.

Binding of CGRP, AM, and AM2 to their cognate class B receptor, the calcitonin receptor-like receptor (CLR), is dependent on association of CLR with one of three accessory membrane proteins that determine ligand selectivity: receptor activity-modifying proteins (RAMPs) 1, 2, or 3. RAMPs have an ECD of about 100 amino acids and a single TM segment. CLR:RAMP1 is a CGRP receptor, CLR:RAMP2 preferentially recognizes AM and is called the $AM_1$ receptor, and CLR:RAMP3 binds both AM and AM2 with high affinities and is called the $AM_2$ receptor. Amy has a low affinity for the class B CT receptor (CTR); however, when CTR associates with any of the RAMPs, its affinity for Amy is markedly increased. CTR alone is the receptor for CT. Thus the RAMPs profoundly alter the behavior of CLR and CTR.

For peptide-based therapeutics targeting the CGRP or AM receptors, selectivity against the CTR and AMY receptors is desired because of their different functions. CTR is involved in calcium homeostasis and bone remodeling. Salmon CT, which has higher affinity for human CTR than human CT, has long been used as a therapeutic for Paget's disease and osteoporosis. Amy signaling controls blood glucose levels and regulates food intake. The Amy analog Pramlintide is used as an insulin adjunct therapy for types I and II diabetes, and AMY activation is explored as an obesity treatment.

Crystal structures have been available for ligand-free and small molecule antagonist-bound CLR:RAMP1 and ligand-free CLR:RAMP2 ECD complexes, but these have provided little insight into how the peptides bind or how RAMPs determine selectivity. In a further complication, it has appeared unlikely that CGRP and AM bind as extended helices as seen with other class B peptide ligands; there is evidence that only a small portion of these peptides form α-helices and that at their C-termini, there are one or more turn structures. A better understanding of the mechanism of binding of CGRP and AM to their respective CLR:RAMP receptor complexes has been desired.

BRIEF DESCRIPTION OF THE DRAWINGS

Several embodiments of the inventive concepts of the present disclosure are illustrated in the appended drawings. It is to be noted, however, that the appended drawings only illustrate several embodiments and are therefore not intended to be considered limiting of the scope of the present disclosure.

FIG. 2(A-C) depicts binding of (A) AM-based peptide AM(37-52)NH$_2$, (B) variant peptides AM(37-52)NH$_2$ [S45W, Q50W], AM(37-52)NH$_2$[Q50F], and AM(37-52) NH$_2$[Q50W], and (C) variant peptides AM(37-52)NH$_2$ [D39K], AM(37-52)NH$_2$[K46L, Q50W], and AM(37-52) NH$_2$[K46L, Q50W, Y52F], to purified CGRP receptor extracellular domain complex. Single representative experiments conducted with duplicate samples are shown. Error bars are S.E.M.

FIG. 2(D-E) depicts binding of (D) variant peptides AM(37-52)NH$_2$[D39F, K46L, Q50W], AM(37-52)NH$_2$ [D39F, K46L, Q50W, Y52F], and AM(37-52)NH$_2$[S45W, K46L, Q50W, Y52F], and (E) variant peptides AM(37-52) NH$_2$[S45W, K46M, Q50W, Y52F], and AM(37-52)NH$_2$ [S45W, K46W, Q50W, Y52F], to purified CGRP receptor extracellular domain complex. Single representative experiments conducted with duplicate samples are shown. Error bars are S.E.M.

FIG. 2(F-H) depicts binding of (F) variant peptides AM(37-52)NH$_2$[S45T, K46W, Q50W], AM(37-52)NH$_2$[S45T, K46L, Q50W], and AM(37-52)NH$_2$[S45W, K46L, S48G, Q50W, Y52F], (G) variant peptide AM(37-52)NH$_2$[S45W, K46L, I47M, Q50W, Y52F], and (H) variant peptides AM(37-52)NH$_2$[S45R, K46W, Q50W], and AM(37-52)NH$_2$[S45R,K46L, Q50W], to purified CGRP receptor extracellular domain complex. Single representative experiments conducted with duplicate samples are shown. Error bars are S.E.M.

FIG. 2(I-J) depicts binding of (I) variant peptides AM(37-52)NH$_2$[S45R, K46W, S48G, Q50W], AM(37-52)NH$_2$[S45R, K46L, S48G, Q50W], and AM(37-52)NH$_2$[S45R, K46W, I47L, S48G, Q50W], and (J) variant peptides AM(37-52)NH$_2$[D39W, Q50W], and AM(37-52)NH$_2$[D37V, S45W, K46L, Q50W, Y52F], to purified CGRP receptor extracellular domain complex. Single representative experiments conducted with duplicate samples are shown. Error bars are S.E.M.

FIG. 3(A-C) depicts binding of (A) AM-based peptide AM(37-52)NH$_2$, and variant peptide AM(37-52)NH$_2$[S45W, Q50W], (B) AM-based peptide AM(37-52)NH$_2$, variant peptide AM(37-52)NH$_2$[Q50F], and variant peptide AM(37-52)NH$_2$[Q50W], and (C) variant peptides AM(37-52)NH$_2$[K46L], AM(37-52)NH$_2$[K46M], and AM(37-52)NH$_2$[D39F], to purified AM$_1$ receptor extracellular domain complex. Single representative experiments conducted with duplicate samples are shown. Error bars are S.E.M.

FIG. 3(D-F) depicts binding of (D) variant peptides AM(37-52)NH$_2$[D39F, K46L, Q50W], AM(37-52)NH$_2$[D39F, K46L, Q50W, Y52F], and AM(37-52)NH$_2$[S45W, K46L, Q50W, Y52F], (E) variant peptides AM(37-52)NH$_2$[[D39K], AM(37-52)NH$_2$[K46L, Q50W], and AM(37-52)NH$_2$[K46L, Q50W, Y52F], and (F) variant peptides AM(37-52)NH$_2$[S45W, K46M, Q50W, Y52F], and AM(37-52)NH$_2$[S45W, K46W, Q50W, Y52F], to purified AM$_1$ receptor extracellular domain complex. Single representative experiments conducted with duplicate samples are shown. Error bars are S.E.M.

FIG. 3(G-H) depicts binding of (G) variant peptides AM(37-52)NH$_2$[S45T, K46W, Q50W], AM(37-52)NH$_2$[S45T, K46L, Q50W], and AM(37-52)NH$_2$[S45W, K46L, S48G, Q50W, Y52F], and (H) variant peptide AM(37-52)NH$_2$[S45W, K46L, I47M, Q50W, Y52F], to purified AM$_1$ receptor extracellular domain complex. Single representative experiments conducted with duplicate samples are shown. Error bars are S.E.M.

FIG. 3(I-K) depicts binding of (I) variant peptides AM(37-52)NH$_2$[S45R, K46W, Q50W], and AM(37-52)NH$_2$[S45R, K46L, Q50W], (J) variant peptides AM(37-52)NH$_2$[S45R, K46W, S48G, Q50W], AM(37-52)NH$_2$[S45R, K46L, S48G, Q50W], and AM(37-52)NH$_2$[S45R, K46W, I47L, S48G, Q50W], and (K) variant peptides AM(37-52)NH$_2$[D39W, Q50W], and AM(37-52)NH$_2$[D37V, S45W, K46L, Q50W, Y52F], to the purified AM$_1$ receptor extracellular domain complex. Single representative experiments conducted with duplicate samples are shown. Error bars are S.E.M.

FIG. 4(A-C) depicts binding of (A) CGRP-based peptide CGRP[8-37]NH$_2$, (B) variant peptides CGRP(27-37)NH$_2$[N31D, S34P, K35F], CGRP(27-37)NH$_2$[N31D, S34P, K35W], and CGRP(27-37)NH$_2$[N31D, S34P, K35F, A36S], and (C) variant peptides CGRP(27-37)NH$_2$[N31D, S34P, K35W, A36S], and CGRP(27-37)NH$_2$[N31D, S34P, K35W, A36S, F37Y], to purified CGRP receptor extracellular domain complex. Single representative experiments conducted with duplicate samples are shown. Error bars are S.E.M.

FIG. 4(D-E) depicts binding of (D) variant peptides CGRP(27-37)NH$_2$[N31D, V32T, S34P, K35W, A36G], and CGRP(27-37)NH$_2$[N31D, V32T, S34P, K35W, A36G, F37Y], and (E) variant peptide CGRP(27-37)NH$_2$[N31D, V32T, S34P, K35W, A36S], to purified CGRP receptor extracellular domain complex. Single representative experiments conducted with duplicate samples are shown. Error bars are S.E.M.

FIG. 5(A-C) depicts binding of (A) CGRP-based peptide CGRP(11-37)NH$_2$, (B) variant peptides CGRP(27-37)NH$_2$[N31D, S34P, K35F], CGRP(27-37)NH$_2$[N31D, S34P, K35W], and CGRP(27-37)NH$_2$[N31D, S34P, K35F, A36S], and (C) variant peptides CGRP(27-37)NH$_2$[N31D, S34P, K35W, A36S], and CGRP(27-37)NH$_2$[N31D, S34P, K35W, A36S, F37Y], to the purified AM$_1$ receptor extracellular domain complex. Single representative experiments conducted with duplicate samples are shown. Error bars are S.E.M.

FIG. 5(D-E) depicts binding of (D) variant peptides CGRP(27-37)NH$_2$[N31D, V32T, S34P, K35W, A36G], and CGRP(27-37)NH$_2$[N31D, V32T, S34P, K35W, A36G, F37Y], and (E) variant peptide CGRP(27-37)NH$_2$[N31D, V32T, S34P, K35W, A36S], to purified AM$_1$ receptor extracellular domain complex. Single representative experiments conducted with duplicate samples are shown. Error bars are S.E.M.

FIG. 7(A-B) depicts antagonism of cAMP signaling at full-length (A) CGRP (RAMP1:CLR) and (B) AM$_1$ (RAMP2:CLR) receptor complexes transiently expressed in COS-7 cells by the variant peptide AM(37-52)NH$_2$[S45W/K46L/Q50W/Y52F]. A single representative experiment conducted with duplicate samples is shown. Error bars are S.E.M.

FIG. 8(A-F) depicts binding of AM-based PS-SPCL library mixtures to purified CGRP (A, C, E) and AM$_1$ (B, D, F) receptor extracellular domain complexes. One of 5 positions of the 16 positions in variant AM(37-52)NH$_2$[Q50W] was optimized for each mixture: (A, B) position 45 optimized; (C, D) position 46 optimized; and (E, F) position 47 optimized. Single experiments conducted with duplicate samples are shown. Error bars are S.E.M. (−) indicates no competitor control.

FIG. 8(G-J) depicts binding of AM-based PS-SPCL library mixtures to purified CGRP (G, I) and AM$_1$ (H, J) receptor extracellular domain complexes. One of 5 positions of the 16 positions in variant AM(37-52)NH$_2$[Q50W] was optimized for each mixture: (G, H) position 48 optimized; and (I, J) position 52 optimized. Single experiments conducted with duplicate samples are shown. Error bars are S.E.M. (−) indicates no competitor control.

FIG. 9(A-C) depicts binding of CGRP-based PS-SPCL library mixtures to purified CGRP receptor extracellular domain complexes. One of 5 positions of the 11 positions in variant CGRP(27-37)NH$_2$[S34P, K35W] was optimized for each mixture: (A) position 31 optimized; (B) position 32 optimized; and (C) position 33 optimized. Single experiments conducted with duplicate samples are shown. Error bars are S.E.M. (−) indicates no competitor control.

FIG. 9(D-E) depicts binding of CGRP-based PS-SPCL library mixtures to purified CGRP receptor extracellular domain complexes. One of 5 positions of the 11 positions in variant CGRP(27-37)NH$_2$[S34P, K35W] was optimized for each mixture: (D) position 36 optimized; and (E) position 37 optimized. Single experiments conducted with duplicate samples are shown. Error bars are S.E.M. (−) indicates no competitor control.

DETAILED DESCRIPTION

Figure 1:
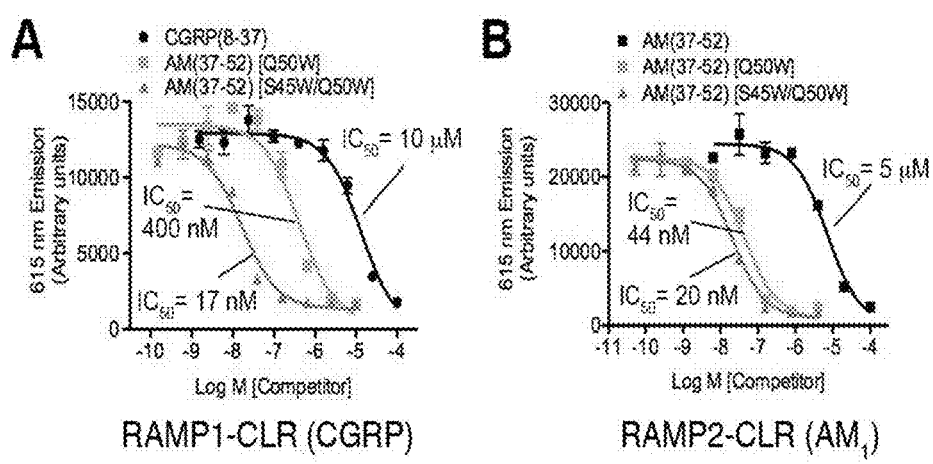
FIG. 1 depicts in (A) binding of a CGRP C-terminal peptide, CGRP(8-37)NH$_2$, and two variant AM C-terminal peptides (AM(37-52)NH$_2$[Q50W] and AM(37-52)NH$_2$[S45W, Q50W]) to purified CGRP receptor extracellular domain complex (CLR:RAMP1). (B) depicts binding of an AM C-terminal peptide, AM(37-52)NH$_2$, and the two variant AM C-terminal peptides to purified AM$_1$ receptor extracellular domain complex (CLR:RAMP2). Single representative experiments conducted with duplicate samples are shown. Error bars are S.E.M.

High-resolution crystal structures of CGRP analog-bound CLR:RAMP1 and AM-bound CLR:RAMP2 ECD heterodimers obtained during the present work revealed bound peptide conformations starkly different from other class B GPCR peptide ligands and helped explain how RAMPs determine peptide selectivity. This work has enabled a better understanding of the mechanism of binding of AM and CGRP to their cognate proteins, enabling the formulation herein of variants of AM, AM2, and CGRP peptides, including (but not limited to) variant AM, AM2, and CGRP peptide fragments that are able to induce antagonistic or enhanced agonistic activity in one or more of the CLR:RAMP receptor complexes for use in treatments of various diseases and conditions involving AM and CGRP receptor proteins. The present disclosure describes such variants and therapeutic methods of their use.

Before further describing various embodiments of the compounds, compositions, and methods of the present disclosure in more detail by way of exemplary description, examples, and results, it is to be understood that the compounds, compositions, and methods of the present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning, and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications, and equivalents apparent to those having ordinary skill in the art are included within the scope of the present disclosure. All of the compounds, compositions, and methods of production and application and use thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions, and/or methods and in the steps or in the sequence of steps of the methods described herein without departing from the concept, spirit, and scope of the inventive concepts.

All patents, published patent applications, and non-patent publications mentioned in the specification or referenced in any portion of this application are herein expressly incorporated by reference in their entirety to the same extent as if each individual patent or publication was specifically and individually indicated to be incorporated by reference.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y, and Z" will be understood to include X alone, Y alone, and Z alone, as well as any combination of X, Y, and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

As used in this specification and claims, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB.

Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately," where used herein when referring to a measurable value such as an amount, a temporal duration, and the like, is meant to encompass, for example, variations of ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds of the present disclosure may be combined with one or more pharmaceutically-acceptable excipients, including carriers, vehicles, and diluents which may improve solubility, deliverability, dispersion, stability, and/or conformational integrity of the compounds or conjugates thereof.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the composition to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. The term "topical" is used herein to define a mode of administration through an epithelial surface, such as but not limited to, the skin, eye, or internal epithelial surfaces. In addition, the compositions of the present disclosure may be designed to provide delayed, controlled, extended, and/or sustained release using formulation techniques which are well known in the art.

The terms "therapeutic composition" and "pharmaceutical composition" refer to a composition containing a peptide as described herein that may be administered to a subject by any method known in the art or otherwise contemplated herein, wherein administration of the composition brings about a therapeutic effect as described elsewhere herein.

The term "effective amount" refers to an amount of a peptide or peptide compound which is sufficient to exhibit a detectable therapeutic, amelioration, or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or a symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

The term "homologous" or "% identity" as used herein means a nucleic acid (or fragment thereof) or a protein (or a fragment thereof) having a degree of homology to the corresponding natural reference nucleic acid or protein that may be in excess of 70%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%. For example, in regard to peptides or polypeptides, the percentage of homology or identity as described herein is typically calculated as the percentage of amino acid residues found in the smaller of the two sequences which align with identical amino acid residues in the sequence being compared, when four gaps in a length of 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul (*Proc. Natl. Acad. Sci. USA* (1990) 87:2264-2268), modified as in Karlin & Altschul (*Proc. Natl. Acad. Sci. USA* (1993) 90:5873-5877).

In one embodiment "% identity" represents the number of amino acids or nucleotides which are identical at corresponding positions in two sequences of a protein having the same activity or encoding similar proteins. For example, two amino acid sequences each having 100 residues will have 95% identity when 95 of the amino acids at corresponding positions are the same.

Another example of a mathematical algorithm used for comparison of sequences is the algorithm of Myers & Miller (CABIOS (1988) 4:11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman (*Proc. Natl. Acad. Sci. USA* (1988) 85:2444-2448).

Another algorithm is the WU-BLAST (Washington University BLAST) version 2.0 software (WU-BLAST version 2.0 executable programs for several UNIX platforms). This program is based on WU-BLAST version 1.4, which in turn is based on the public domain NCBI-BLAST version 1.4 (Altschul & Gish, *Methods in Enzymology* (1996) 266:460-480; Altschul et al., *J Molec Biol.* (1990) 215:403-410; Gish & States, *Nature Genetics* (1993) 3:266-272; Karlin & Altschul, *Proc. Natl. Acad. Sci. USA* (1993) 90:5873-5877; all of which are incorporated by reference herein).

In addition to those otherwise mentioned herein, mention is made also of the programs BLAST, gapped BLAST, BLASTN, BLASTP, and PSI-BLAST, provided by the National Center for Biotechnology Information. These programs are widely used in the art for this purpose and can align homologous regions of two amino acid sequences. In all search programs in the suite, the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Specific amino acids may be referred to herein by the following designations: alanine: ala or A; arginine: arg or R; asparagine: asn or N; aspartic acid: asp or D; cysteine: cys or C; glutamic acid: glu or E; glutamine: gln or Q; glycine: gly or G; histidine: his or H; isoleucine: ile or I; leucine: leu or L; lysine: lys or K; methionine: met or M; phenylalanine: phe or F; proline: pro or P; serine: ser or S; threonine: thr or T; tryptophan: trp or W; tyrosine: tyr or Y; and valine: val or V.

The terms "polynucleotide sequence" or "nucleic acid," as used herein, include any polynucleotide sequence which encodes a mutant peptide including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a mutant peptide, or encoding a therapeutically-effective fragment of a mutant peptide can be substantially the same as the coding sequence of the endogenous coding sequence as long as it encodes a biologically active mutant peptide. Further, the mutant peptide, or therapeutically-effective fragment of a mutant peptide may be expressed using polynucleotide sequence(s) which differ in codon usage due to the degeneracies of the genetic code or allelic variations. Moreover, the mutant peptides of the presently disclosed inventive concepts and the nucleic acids which encode them include peptide and nucleic acid variants which comprise additional conservative substitutions. For example, the variant peptides include, but are not limited to, variants that are not exactly the same as the sequences disclosed herein, but which have, in addition to the substitutions explicitly described for various sequences listed herein, conservative substitutions of amino acid residues which do substantially not impair the agonistic or antagonistic activity or properties of the variants described herein. Examples of such conservative amino acid substitutions include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met.

Where referred to herein, the terms "variant" and "mutant" are used interchangeably. A variant peptide, peptide variant, or mutant refers to any peptide described herein, including fragments thereof, comprising at least one amino acid substitution in the wild type amino acid sequence or in a fragment thereof. Non-limiting examples of such variant peptides are described in further detail below.

Where used herein, the term CLR:RAMP1 refers to the CGRP receptor, CLR:RAMP2 refers to the $AM_1$ receptor, and CLR:RAMP3 refers to the $AM_2$ receptor.

Where used herein the term "fragment" refers to a portion of a complete amino acid sequence or nucleic acid sequence. For example, a fragment of wild type AM (SEQ ID NO:1) refers, in at least certain embodiments, to a peptide having 5 or more contiguous amino acids of wild type AM, for example, 5, 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 amino acids. A fragment of wild type CGRP (SEQ ID NOs: 31 and 32) refers, in at least certain embodiments, to a peptide having 4 or more contiguous amino acids of wild type α-CGRP or wild type β-CGRP, for example, 4, 5, 6, 7, 8, 9, 10, 11, 12 13, 14, 15, 16, 17, 18, 19, 20, 21, 22, 23, 24, 25, 26, 27, 28, 29, 30, 31, 32, or 33 amino acids. A fragment of wild type AM2/intermedin (SEQ ID NO:47) refers, in at least certain embodiments, to a peptide having 5 or more contiguous amino acids of wild type AM2/intermedin, for example, 5, 6, 7, 8, 9, 10, 11, 12 13, 14, 15, 16, 17, 18, 19, 20, 21, 22, 23, 24, 25, 26, 27, 28, 29, 30, 31, or 32 amino acids.

Non-limiting embodiments of variant peptides of the present disclosure are included in specific examples shown below, which comprise just a small subset of the variant peptides supported and enabled herein. In all specific sequences below except SEQ ID NO:48, the C-terminal residue is amidated (i.e., the C-terminal OH group is replaced by $NH_2$), e.g., in SEQ ID NOs:1-47 and 49-52 the Y or F is amidated. In SEQ ID NOs: 53 and 54, the C-terminal residue is also amidated.

Wild-type human adrenomedullin (($AM(1-52)-NH_2$)) is a 52 amino acid, C-terminally-amidated peptide having the sequence:

YRQSMNNFQGLRSFGCRFGTCTVQKLAHQIYQFT-DKDKDNVAPRSKISPQGY (SEQ ID NO:1), with a disulfide bond between C16 and C21.

AM (13-52)-$NH_2$ is a fragment of SEQ ID NO:1 having the sequence:

SFGCRFGTCTVQKLAHQIYQFTDKDKDNVAPR-SKISPQGY (SEQ ID NO:2), with a disulfide bond between the two cysteines.

AM (22-52)-$NH_2$ is a C-terminal fragment of SEQ ID NO:1 having the sequence:

TVQKLAHQIYQFTDKDKDNVAPRSKISPQGY (SEQ ID NO:3),

AM (37-52)-$NH_2$ is a C-terminal fragment of SEQ ID NO:1 having the sequence:

DKDNVAPRSKISPQGY (SEQ ID NO:4).

SEQ ID NOS: 5-30 below are mutants of SEQ ID NO:4 (C-terminal amino acids 37-52 of SEQ ID NO:1). Novel aspects of the present disclosure include, but are not limited to, the following specific variant peptides based on AM:

AM(37-52)$NH_2$ [Q50F]:
DKDNVAPRSKISPFGY; (SEQ ID NO: 5)

AM(37-52)$NH_2$ [Q50W]:
DKDNVAPRSKISPWGY; (SEQ ID NO: 6)

AM(37-52)$NH_2$ [K46L]:
DKDNVAPRSLISPQGY; (SEQ ID NO: 7)

AM(37-52)$NH_2$ [K46M]:
DKDNVAPRSMISPQGY; (SEQ ID NO: 8)

AM(37-52)$NH_2$ [K46W]:
DKDNVAPRSWISPQGY; (SEQ ID NO: 9)

AM(37-52)$NH_2$ [D39K]:
DKKNVAPRSKISPQGY; (SEQ ID NO: 10)

AM(37-52)$NH_2$ [S45W, Q50W]:
DKDNVAPRWKISPWGY; (SEQ ID NO: 11)

AM(37-52)$NH_2$ [K46L, Q50W]:
DKDNVAPRSLISPWGY; (SEQ ID NO: 12)

AM(37-52)$NH_2$ [D39W, Q50W]:
DKWNVAPRSKISPWGY; (SEQ ID NO: 13)

AM(37-52)$NH_2$ [D39K, Q50F]:
DKKNVAPRSKISPFGY; (SEQ ID NO: 14)

AM(37-52)$NH_2$ [D39K, Q50W]:
DKKNVAPRSKISPWGY; (SEQ ID NO: 15)

AM(37-52)$NH_2$ [K46L, Q50W, Y52F]:
DKDNVAPRSLISPWGF; (SEQ ID NO: 16)

AM(37-52)$NH_2$ [D39F, K46L, Q50W]:
DKFNVAPRSLISPWGY; (SEQ ID NO: 17)

AM(37-52)$NH_2$ [S45R, K46W, Q50W]:
DKDNVAPRRWISPWGY; (SEQ ID NO: 18)

AM(37-52)$NH_2$ [S45R, K46L, Q50W]:
DKDNVAPRRLISPWGY; (SEQ ID NO: 19)

AM(37-52)$NH_2$ [D39F, K46L, Q50W, Y52F]:
DKFNVAPRSLISPWGF; (SEQ ID NO: 20)

AM(37-52)$NH_2$ [S45W, K46W, Q50W, Y52F]:
DKDNVAPRWWISPWGF; (SEQ ID NO: 21)

AM(37-52)$NH_2$ [S45W, K46L, Q50W, Y52F]:
DKDNVAPRWLISPWGF; (SEQ ID NO: 22)

AM(37-52)$NH_2$ [S45W, K46M, Q50W, Y52F]:
DKDNVAPRWMISPWGF; (SEQ ID NO: 23)

AM(37-52)$NH_2$ [S45R, K46W, S48G, Q50W]:
DKDNVAPRRWIGPWGY; (SEQ ID NO: 24)

-continued

AM(37-52)NH₂ [S45R, K46L, S48G, Q50W]:
(SEQ ID NO: 25)
DKDNVAPRRLIGPWGY;

AM(37-52)NH₂ [D37V, S45W, K46L, Q50W, Y52F]:
(SEQ ID NO: 26)
VKDNVAPRWLISPWGF;

AM(37-52)NH₂ [S45W, K46L, S48G, Q50W, Y52F]:
(SEQ ID NO: 27)
DKDNVAPRWLIGPWGF;

AM(37-52)NH2 [S45W, K46L, I47M, Q50W, Y52F]:
(SEQ ID NO: 28)
DKDNVAPRWLMSPWGF;

AM(37-52)NH2 [S45R, K46W, I47L, S48G, Q50W]:
(SEQ ID NO: 29)
DKDNVAPRRWLGPWGY;
and

AM(37-52)NH2 [D39K, S45R, K46L, S48G, Q50W]:
(SEQ ID NO: 30)
DKKNVAPRRLIGPWGY.

Wild type human Calcitonin gene-related peptide (α-CGRP) is a 37 amino acid, C-terminally-amidated peptide having the sequence:
ACDTATCVTHRLAGLLSRSGGVVKNNFVPTNVG-SKAF (SEQ ID NO:31), with a disulfide bond between the two cysteines.

Wild type human Calcitonin gene-related peptide (β-CGRP) is a 37 amino acid, C-terminally-amidated peptide having the sequence:
ACNTATCVTHRLAGLLSRSGGMVKSNFVPTNVG-SKAF (SEQ ID NO:32), with a disulfide bond between the two cysteines.

CGRP(8-37)NH₂ is a 30 amino acid fragment of SEQ ID NO:31 having the sequence:
VTHRLAGLLSRSGGVVKNNFVPTNVGSKAF (SEQ ID NO:33).

CGRP(27-37)NH₂ is an 11 amino acid C-terminal fragment of SEQ ID NO:31 having the sequence: FVPTNVG-SKAF (SEQ ID NO:34).

FVPTDVGPFAF (SEQ ID NO:35) is a sequence published in Rist et al. (*J Med Chem*. (1998) 41(1):117-23).

Variant peptides having sequences SEQ ID NOS: 36-43 below are mutants of SEQ ID NO:34 (amino acids 27-37 of SEQ ID NO:31). Novel aspects of the present disclosure include, but are not limited to, the following specific variant peptides based on wild-type human α-CGRP and β-CGRP:

CGRP(27-37)NH₂ [N31D, S34P, K35W]:
(SEQ ID NO: 36)
FVPTDVGPWAF;

CGRP(27-37)NH₂ [N31D, S34P, K35W, F37Y]:
(SEQ ID NO: 37)
FVPTDVGPWAY;

CGRP(27-37)NH₂ [N31D, S34P, K35F, A36S]:
(SEQ ID NO: 38)
FVPTDVGPFSF;

CGRP(27-37)NH₂ [N31D, S34P, K35W, A36S]:
(SEQ ID NO: 39)
FVPTDVGPWSF;

CGRP(27-37)NH₂ [N31D, S34P, K35W, A36S, F37Y]:
(SEQ ID NO: 40)
FVPTDVGPWSY;

-continued

CGRP(27-37)NH₂ [N31D, V32T, S34P, K35W, A36G]:
(SEQ ID NO: 41)
FVPTDTGPWGF;

CGRP(27-37)NH₂ [N31D, V32T, S34P, K35W, A36S]:
(SEQ ID NO: 42)
FVPTDTGPWSF;
and

CGRP(27-37)NH₂ [N31D, V32T, S34P, K35W, A36G, F37Y]:
(SEQ ID NO: 43)
FVPTDTGPWGY.

Variant peptides having SEQ ID NOS: 44-46 below are mutants of the fragment comprising amino acids 30-37 of SEQ ID NO:31. Novel aspects of the present disclosure include, but are not limited to, the following specific variant peptides based on wild-type human α-CGRP and β-CGRP:

CGRP(30-37)NH₂ [N31D, S34P, K35W]:
(SEQ ID NO: 44)
TDVGPWAF;

CGRP(30-37)NH₂ [N31D, S34P, K35W, A36S]:
(SEQ ID NO: 45)
TDVGPWSF;
and

CGRP(30-37)NH₂ [N31D, S34P, K35W, A36S, F37Y]:
(SEQ ID NO: 46)
TDVGPWSY.

Wild-type human adrenomedullin-2 (AM2)/intermedin is a 40 amino acid, C-terminally-amidated peptide having the sequence:
VGCVLGTCQVQNLSHRLWQLMGPAGRQD-SAPVDPSSPHSY (SEQ ID NO:47), with a disulfide bond between the two cysteines.

AM2/intermedin (1-24) is a fragment comprising the 24 N-terminal amino acids of AM2/intermedin and having the sequence:
VGCVLGTCQVQNLSHRLWQLMGPA (SEQ ID. NO:48).

Embodiments of the present disclosure also include, but are not limited to, variants of entire AM (SEQ ID NO:1), variant fragments thereof, and/or chimeric peptides comprising such variant fragments. Non-limiting examples of such variant fragments are represented by the structure of Formula I (SEQ ID NO:49), which is based on amino acids 37-52 of SEQ ID NO:1, and the structure of Formula II (SEQ ID NO:50), which is based on amino acids 42-52 of SEQ ID NO:1.

$$X_1\text{-}K\text{-}X_3\text{-}N\text{-}V\text{-}A\text{-}P\text{-}R\text{-}X_9\text{-}X_{10}\text{-}X_{11}\text{-}X_{12}\text{-}P\text{-}X_{14}\text{-}G\text{-}X_{16} \quad (I)$$

wherein
$X_1$ is A, D, V, L, or I,
$X_3$ is D, F, M, Y, V, I, E, K, W, L, or R,
$X_9$ is S, W, Y, F, R, T, or L,
$X_{10}$ is K, G, L, M, Y, A, W, or F,
$X_{11}$ is I, L, or M,
$X_{12}$ is S, T, or G,
$X_{14}$ is Q, F, Y, W, or H, and
$X_{16}$ is Y or F, and wherein the Y or F is amidated.

The peptides having the structure of Formula I may optionally be extended at the N-terminus by all or any portion of amino acids 1-36 of SEQ ID NO:1, all or any portion of amino acids 1-22 of SEQ ID NO:31, all or any portion of amino acids 1-22 of SEQ ID NO:32, or all or any portion of amino acids 1-24 of SEQ ID NO:47; and with the proviso that the variant peptide does not include a sequence comprising positions 37-52 of SEQ ID NO:1. Examples of such extended portions include, but are not limited to, amino acids 13-36 of SEQ ID NO:1 and amino acids 1-22 of SEQ ID NOs:31 or 32.

$$A\text{-}P\text{-}R\text{-}X_4\text{-}X_5\text{-}X_6\text{-}X_7\text{-}P\text{-}X_9\text{-}G\text{-}X_{11} \tag{II}$$

wherein
$X_4$ is S, W, Y, F, R, T, or L,
$X_5$ is K, G, L, M, Y, A, W, or F,
$X_6$ is I, L, or M,
$X_7$ is S, T, or G,
$X_9$ is Q, F, Y, W, or H, and
$X_{11}$ is Y or F, wherein the Y or F is amidated.

The peptides having the structure of Formula II may optionally be extended at the N-terminus by all or any portion of amino acids 1-41 of SEQ ID NO:1, all or any portion of amino acids 1-26 of SEQ ID NO:31, all or any portion of amino acids 1-26 of SEQ ID NO:32, or all or any portion of amino acids 1-29 of SEQ ID NO:47; and with the proviso that the variant peptide does not include a sequence comprising positions 42-52 of SEQ ID NO:1. Examples of such extended portions include, but are not limited to, amino acids 13-41 of SEQ ID NO:1 and amino acids 1-26 of SEQ ID NOs:31 or 32.

Embodiments of the present disclosure also include, but are not limited to, variants of entire α-CGRP (SEQ ID NO:31) and β-CGRP (SEQ ID NO:32), variant fragments thereof, and/or chimeric proteins comprising such variant fragments. Non-limiting examples of such variant fragments are represented by the structure of Formula III (SEQ ID NO:51), which is based on amino acids 27-37 of SEQ ID NO:31, and the structure of Formula IV (SEQ ID NO:52), which is based on amino acids 30-37 of SEQ ID NO:31:

$$F\text{-}V\text{-}P\text{-}T\text{-}X_5\text{-}X_6\text{-}G\text{-}X_8\text{-}X_9\text{-}X_{10}\text{-}X_{11} \tag{III}$$

wherein
$X_5$ is N, D, or W,
$X_6$ is V, T, or W,
$X_8$ is P or S,
$X_9$ is W, Y, or H,
$X_{10}$ is A, S, or G,
$X_{11}$ is F or Y, wherein F or Y is amidated.

The peptides having the structure of Formula III may optionally be extended at the N-terminus by all or any portion of amino acids 1-41 of SEQ ID NO:1, all or any portion of amino acids 1-26 of SEQ ID NO:31, all or any portion of amino acids 1-26 of SEQ ID NO:32, or all or any portion of amino acids 1-29 of SEQ ID NO:47. Examples of such extended portions include, but are not limited to, amino acids 13-41 of SEQ ID NO:1 and amino acids 1-26 of SEQ ID NOs:31 or 32.

$$T\text{-}X_2\text{-}X_3\text{-}G\text{-}X_5\text{-}X_6\text{-}X_7\text{-}X_8 \tag{IV}$$

wherein
$X_2$ is N, D, or W,
$X_3$ is V, T, or W,
$X_5$ is P or S,
$X_6$ is W, Y, or H,
$X_7$ is A, S, or G,
$X_8$ is F or Y, wherein the F or Y is amidated.

The peptides having the structure of Formula IV may optionally be extended at the N-terminus by all or any portion of amino acids 1-44 of SEQ ID NO:1, all or any portion of amino acids 1-29 of SEQ ID NO:31, all or any portion of amino acids 1-29 of SEQ ID NO:32, or all or any portion of amino acids 1-32 of SEQ ID NO:47. Examples of such extended portions include, but are not limited to, amino acids 13-44 of SEQ ID NO:1 and amino acids 1-23 or 1-29 of SEQ ID NOs:31 or 32.

The amino acid sequence having a structure as represented by Formula V below was used to create variant peptide positional libraries (see FIG. 8) based on positions 37-52 of AM:

$$D\text{-}K\text{-}D\text{-}N\text{-}V\text{-}A\text{-}P\text{-}R\text{-}X_9\text{-}X_{10}\text{-}X_{11}\text{-}X_{12}\text{-}P\text{-}W\text{-}G\text{-}X_{16} \tag{V}$$

wherein
$X_9$ is A, R, N, D, E, Q, G, H, I, L, K, M, F, P, S, T, W, Y, or V,
$X_{10}$ is A, R, N, D, E, Q, G, H, I, L, K, M, F, P, S, T, W, Y, or V,
$X_{11}$ is A, R, N, D, E, Q, G, H, I, L, K, M, F, P, S, T, W, Y, or V,
$X_{12}$ is A, R, N, D, E, Q, G, H, I, L, K, M, F, P, S, T, W, Y, or V, and
$X_{16}$ is A, R, N, D, E, Q, G, H, I, L, K, M, F, P, S, T, W, Y, or V, wherein $X_{16}$ is amidated.

The amino acid sequence having a structure as represented by Formula VI below was used to create variant peptide positional libraries (see FIG. 9) based on positions 27-37 of CGRP:

$$F\text{-}V\text{-}P\text{-}T\text{-}X_5\text{-}X_6\text{-}X_7\text{-}P\text{-}W\text{-}X_{10}\text{-}X_{11} \tag{VI}$$

wherein
$X_5$ is A, R, N, D, E, Q, G, H, I, L, K, M, F, P, S, T, W, Y, or V,
$X_6$ is A, R, N, D, E, Q, G, H, I, L, K, M, F, P, S, T, W, Y, or V,
$X_7$ is A, R, N, D, E, Q, G, H, I, L, K, M, F, P, S, T, W, Y, or V,
$X_{10}$ is A, R, N, D, E, Q, G, H, I, L, K, M, F, P, S, T, W, Y, or V, and
$X_{11}$ is A, R, N, D, E, Q, G, H, I, L, K, M, F, P, S, T, W, Y, or V, wherein $X_{11}$ is amidated.

In at least certain embodiments, the present disclosure includes a variant peptide, optionally consisting of up to 70 amino acids, that binds to at least one receptor complex of the group consisting of CLR:RAMP1, CLR:RAMP2, and CLR:RAMP3, the variant peptide having an affinity $K_i$ for the receptor complex of less than about 1 μM, the peptide having a structure as represented by Formula I (SEQ ID NO:49):

$$X_1\text{-}K\text{-}X_3\text{-}N\text{-}V\text{-}A\text{-}P\text{-}R\text{-}X_9\text{-}X_{10}\text{-}X_{11}\text{-}X_{12}\text{-}P\text{-}X_{14}\text{-}G\text{-}X_{16} \tag{I}$$

wherein:
$X_1$ is A, D, V, L, or I,
$X_3$ is D, F, M, Y, V, I, E, K, W, L, or R,
$X_9$ is S, W, Y, F, R, T, or L,
$X_{10}$ is K, G, L, M, Y, A, W, or F,
$X_{11}$ is I, L, or M,
$X_{12}$ is S, T, or G,
$X_{14}$ is Q, F, Y, W, or H, and
$X_{16}$ is Y or F, wherein the Y or F is amidated;

wherein the variant peptide is optionally extended at the N-terminus by all or any portion of amino acids 1-36 of SEQ ID NO:1, by all or any portion of amino acids 1-22 of SEQ ID NO:31, by all or any portion of amino acids 1-22 of SEQ ID NO:32, or by all or any portion of amino acids 1-24 of SEQ ID NO:47; and with the proviso that the variant peptide does not include a contiguous sequence comprising the amino acids in positions 37-52 of SEQ ID NO:1.

In certain embodiments, the variant peptide of Formula I has agonistic activity for the at least one receptor complex. In certain other embodiments, the variant peptide of Formula I has antagonistic activity for the at least one receptor complex. The variant peptide may be bound to a carrier molecule directly or indirectly via a linker molecule.

In at least certain embodiments, the present disclosure includes a variant peptide, optionally consisting of up to 70 amino acids, that binds to at least one receptor complex of the group consisting of CLR:RAMP1, CLR:RAMP2, and CLR:RAMP3, the variant peptide having an affinity $K_i$ for the receptor complex of less than about 1 µM, the peptide having a structure as represented by Formula II (SEQ ID NO:50):

$$A-P-R-X_4-X_5-X_6-X_7-P-X_9-G-X_{11} \quad (II)$$

wherein:
$X_4$ is S, W, Y, F, R, T, or L,
$X_5$ is K, G, L, M, Y, A, W, or F,
$X_6$ is I, L, or M,
$X_7$ is S, T, or G,
$X_9$ is Q, F, Y, W, or H, and
$X_{11}$ is Y or F, wherein the Y or F is amidated;
wherein the peptide is optionally extended at the N-terminus by all or any portion of amino acids 1-41 of SEQ ID NO:1, by all or any portion of amino acids 1-26 of SEQ ID NO:31, by all or any portion of amino acids 1-26 of SEQ ID NO:32, or by all or any portion of amino acids 1-29 of SEQ ID NO:47; and with the proviso that the variant peptide does not include a contiguous sequence comprising the amino acids in positions 42-52 of SEQ ID NO:1.

In certain embodiments, the variant peptide of Formula II has agonistic activity for the at least one receptor complex. In certain other embodiments, the variant peptide of Formula II has antagonistic activity for the at least one receptor complex. The variant peptide may be bound to a carrier molecule directly or indirectly via a linker molecule.

In at least certain embodiments, the present disclosure includes a variant peptide, optionally consisting of up to 70 amino acids, that binds to at least one receptor complex of the group consisting of CLR:RAMP1, CLR:RAMP2, and CLR:RAMP3, the variant peptide having an affinity $K_i$ for the receptor complex of less than about 1 µM, the peptide having a structure as represented by Formula III (SEQ ID NO:51):

$$F-V-P-T-X_5-X_6-G-X_8-X_9-X_{10}-X_{11} \quad (III)$$

wherein:
$X_5$ is N, D, or W,
$X_6$ is V, T, or W,
$X_8$ is P or S,
$X_9$ is W, Y, or H,
$X_{10}$ is A, S, or G,
$X_{11}$ is F or Y, wherein the F or Y is amidated;
wherein the peptide is optionally extended at the N-terminus by all or any portion of amino acids 1-41 of SEQ ID NO:1, by all or any portion of amino acids 1-26 of SEQ ID NO:31, by all or any portion of amino acids 1-26 of SEQ ID NO:32, or by all or any portion of amino acids 1-29 of SEQ ID NO:47.

In certain embodiments, the variant peptide of Formula III has agonistic activity for the at least one receptor complex. In certain other embodiments, the variant peptide of Formula III has antagonistic activity for the at least one receptor complex. The variant peptide may be bound to a carrier molecule directly or indirectly via a linker molecule.

In at least certain embodiments, the present disclosure includes a variant peptide, optionally consisting of up to 70 amino acids, that binds to at least one receptor complex of the group consisting of CLR:RAMP1, CLR:RAMP2, and CLR:RAMP3, the variant peptide having an affinity $K_i$ for the receptor complex of less than about 1 µM, the peptide having a structure of Formula IV (SEQ ID NO:52):

$$T-X_2-X_3-G-X_5-X_6-X_7-X_8 \quad (IV)$$

wherein:
$X_2$ is N, D, or W,
$X_3$ is V, T, or W,
$X_5$ is P or S,
$X_6$ is W, Y, or H,
$X_7$ is A, S, or G,
$X_8$ is F or Y, wherein the F or Y is amidated;
wherein the peptide is optionally extended at the N-terminus by all or any portion of amino acids 1-44 of SEQ ID NO:1, by all or any portion of amino acids 1-29 of SEQ ID NO:31, by all or any portion of amino acids 1-29 of SEQ ID NO:32, or by all or any portion of amino acids 1-32 of SEQ ID NO:47.

In certain embodiments, the variant peptide of Formula IV has agonistic activity for the at least one receptor complex. In certain other embodiments, the variant peptide of Formula IV has antagonistic activity for the at least one receptor complex. The variant peptide may be bound to a carrier molecule, directly, or indirectly via a linker molecule.

As noted above, in certain embodiments, the variant peptides of the present disclosure (e.g., peptides comprising sequences constructed according to Formulas I-IV) can be linked, conjugated, complexed, bound, coupled, or otherwise attached to a carrier molecule, such as a protein or polymeric material such as polyethylene glycol (PEG) via PEGylation. For example, the variant peptides may be conjugated or otherwise attached to a suitable carrier molecule such as, but not limited to, keyhole limpet haemocyanin (KLH), ovalbumin, bovine serum albumin (BSA), or human serum albumin (HSA). Other examples of carrier proteins which may be used include, but are not limited to, those disclosed in US Published Patent Applications 2013/0072881, 2013/0209503, and 2013/0337006, the disclosures of which are expressly incorporated herein by reference. The variant peptide may be bound directly to the carrier molecule or linked via a linker compound or linker peptide, for example as described in the US Published Patent Applications 2013/0072881, 2013/0209503, and 2013/0337006.

As noted above, the variant peptides of the present disclosure (e.g., peptides comprising sequences constructed according to Formulas I-IV) can be used to treat a number of conditions and diseases involving the CGRP and AM receptor complexes CLR:RAMP1, CLR:RAMP2, and CLR:RAMP3. Examples of conditions and diseases that can be treated in a subject by the administration of a variant peptide of the present disclosure which has AM receptor antagonistic activity include, but are not limited to: Prostate cancer, Glioblastoma, Lewis lung carcinoma, Cervical cancer, Melanoma, Breast cancer, Colon cancer, Ovarian cancer, and Sepsis. Examples of conditions and diseases that can be treated in a subject by the administration of a variant peptide of the present disclosure which has AM receptor agonistic activity include, but are not limited to: Ulcerative colitis, Crohn's disease, Inflammatory bowel disease, Myocardial infarction, Heart failure, Atherosclerotic vascular disease, Tissue or organ ischemia, Arteriosclerosis obliterans, Buerger's disease, Ischemic brain injury, Pulmonary hypertension, Sepsis, Lymphedema (primary and secondary), Promotion of embryo implantation during in vitro fertilization, and Preeclampsia. Examples of conditions and diseases that can be treated in a subject by the administration of a variant peptide of the present disclosure which has CGRP receptor antagonistic activity include, but are not limited to: Migraine headache, Hyperalgesia, Menopausal hot flashes, Arthritis (both osteoarthritis and rheumatoid arthritis), and Sepsis. Examples of conditions and diseases that can be treated in a subject by the administration of a variant peptide of the present disclosure which has CGRP receptor agonistic activity include, but are not limited to: Pulmonary hypertension, Heart failure, Atherosclerosis, sepsis, Myocardial ischemia, gut ischemia, liver ischemia, kidney ischemia, and brain ischemia.

The embodiments of the present disclosure will be more readily understood by reference to the following examples and embodiments, which are included merely for purposes of illustration of certain aspects and embodiments of the inventive concepts, and are not intended to be limiting. The following detailed examples and methods describe how to make and use the various mutant peptides of the present disclosure and are to be construed, as noted above, only as illustrative, and not limitations of the disclosure in any way whatsoever. Those skilled in the art will promptly recognize appropriate variations from the materials and procedures described herein.

Example

Methods

Protein production and characterization and peptides. Plasmid construction, mutagenesis, protein expression, purification, and the AlphaScreen® peptide binding assay (Perkin-Elmer, Waltham, Mass.) were performed as previously described with minor modifications to the AlphaScreen® assay (Hill and Pioszak, *Protein expression and purification* (2013) 88:107-113; and Moad and Pioszak, *Protein Sci.* (2013) 22:1775-85). Synthetic peptides were from RS Synthesis (Louisville, Ky.), Bachem (Bubendorf, Switzerland), or were synthesized in-house. Bacterial pETDuet1 expression plasmids encoding tethered MBP-hRAMP1.24-111-(Gly-Ser-Ala)$_3$-hCLR.29-144-H$_6$ and MBP-hRAMP2.55-140-(Gly-Ser-Ala)$_3$-hCLR.29-144-H$_6$ (amino acid numbers indicated) fusion proteins co-expressed with DsbC were constructed using the Gibson Assembly cloning method with Gibson Assembly master mix (New England Biolabs, Ipswich, Mass.). Plasmids for expression of tagged full-length CLR and RAMP1 or RAMP2 receptors in mammalian cells were previously described (Barwell et al., *Peptides* (2010) 31:170-176; Watkins et al., *Br J Pharmacol* (2014) 171:772-788). Site directed mutagenesis was performed with the QuikChange II kit (Agilent Technologies, Santa Clara, Calif.) or using the Gibson Assembly method. All constructs were verified by automated DNA sequencing.

The tethered ECD fusion proteins were expressed in *E. coli*, purified, and characterized for peptide binding with an AlphaScreen® peptide binding assay (Perkin-Elmer, Waltham, Mass.) as previously described (Moad and Pioszak, *Protein Sci.* (2013) 22:1775-85), except that the AlphaScreen® competition assays also included 0.3% (v/v) Triton X-100 in the reaction buffer. Triton X-100 minimized, but did not completely prevent, apparent aggregation of the CGRP(27-37)NH$_2$[N31D,S34P,K35F] peptide (SEQ ID NO:35) that was surprisingly observed only with the MBP-hRAMP1.24-111-(Gly-Ser-Ala)$_3$-hCLR.29-144-H$_6$ protein and not with MBP-hRAMP1.24-111-(Gly-Ser)$_5$-hCLR.29-144-H$_6$ or MBP-hRAMP2.55-140 [L106R]-(Gly-Ser-Ala)$_3$-hCLR.29-144-H$_6$ proteins (data not shown). The apparent aggregation of the CGRP analog prevented it from fully competing the binding signal to background levels, and hence the reported IC$_{50}$ values for the CGRP analog peptides binding to the CGRP receptor crystallization construct are likely a bit higher than the true values. Competitor peptide concentrations higher than 200 µM were avoided because some of the peptides began to exhibit non-specific inhibition at concentrations >200 µM as assessed in control reactions in which the donor and acceptor beads were brought together by a Biotin-(Gly)$_6$-(His)$_6$ peptide. The binding experiments were conducted at least three times with each independent experiment performed with duplicate samples. pIC$_{50}$ values are stated as the mean of the replicate independent experiments ±S.E.M. Although slight variation in pIC$_{50}$ values for a given peptide in assays conducted on different days was occasionally observed, the rank order of IC$_{50}$ values for the various peptides and the magnitude of their differences were very reproducible.

Fluorescence polarization peptide binding assay. The ability of the indicated peptides to displace a FITC-Ahx-AM (37-52)NH$_2$[S45W/Q50W] probe (7 nM) from purified MBP-RAMP1 ECD-(GS)$_5$-CLR ECD-H$_6$ fusion protein (15 nM) or from purified MBP-RAMP2 ECD [L106R]-(GS)$_5$-CLR ECD-H$_6$ fusion protein (110 nM) was assessed by fluorescence polarization (anisotropy). The reactions (50 µL) were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 50 mM HEPES, pH 7.5, 150 mM NaCl, 0.5 mg/ml fatty acid-free BSA, 0.5 mM EDTA, 0.5 mM maltose. K$_I$ values were calculated using nonlinear regression fitting of the competition curves to the exact analytical equations of Roehrl et al. (*Biochemistry* (2004) 43:16056-66) using GraphPad Prism 5.0 (GraphPad Software, San Diego Calif.).

Peptides. Custom synthetic peptides or peptide libraries for binding studies and crystallization were obtained from RS Synthesis (Louisville, Ky.) except the CGRP(27-37)NH$_2$ [N31D,S34P,K35F] peptide used for crystallization, which was assembled by Fmoc SPPS on Rink amide polystyrene resin using a Tribute synthesizer (Protein Technologies, Tucson, Ariz.) with 20% (v/v) piperidine in DMF as Fmoc deblocking reagent (2×5 mins) and HATU/DIPEA (20 mins) as coupling reagents. The peptide was cleaved from the resin with concomitant removal of side chain protecting groups with 95% TFA/2.5% TIPS/2.5% water (v/v/v) for 2 hours and recovered by precipitation into cold diethyl ether and isolated by centrifugation (221 mg). Purification of a portion (110 mg) by RP-HPLC on a C18 column (Waters Xterra, 19×300 mm) afforded the title compound (27.4 mg, >95% purity by HPLC), observed mass (ESI+) (M+H)$^{1+}$=1195.0, calculated mass 1196.4. For cell-based assays human AM(1-52) was from Bachem (Bubendorf, Switzerland) and human αCGRP(1-37) was synthesized in-house (PWH) or was from Bachem.

Crystallization, structure solution, and homology modeling. The tethered MBP-RAMP1 ECD-CLR ECD and MBP-RAMP2 ECD [L106R]-CLR ECD proteins were complexed with CGRP(27-37)NH$_2$[N31D,S34P,K35F] (SEQ ID NO:35) or AM(25-52)NH$_2$ (amino acids 25-52 of SEQ ID NO:1) and crystallized with a reservoir solution of 22% PEG3350, 8% Tacsimate, pH 6.0 for the CGRP receptor complex or 19% PEG3350, 0.1 M Tris-HCl, pH 8.3, 225 mM sodium acetate, and 20% ethylene glycol for the AM$_1$ receptor complex. Diffraction data collected at the APS synchrotron (Argonne, Ill.) were processed with HKL2000 (Otwinowski and Minor, (1997) Processing of X-ray diffraction data collected in oscillation mode. In *Methods in Enzymology*, C. W. J. Carter, and R. M. Sweet, eds. (New York: Academic Press), pp. 307-326.) and the CCP4 suite (Winn et al., *Acta Crystallogr D Biol Crystallogr* (2011) 67:235-242). The structures were solved by molecular replacement with Phaser (McCoy et al., *J Appl Crystallogr* (2007) 40:658-674), rebuilt with COOT (Emsley et al., *Acta Crystallogr D Biol Crystallogr* (2010) 66:486-501), and refined with REFMACS (Murshudov et al., *Acta Crystallogr D Biol Crystallogr* (1997) 53:240-255).

The tethered MBP-RAMP1 ECD-CLR ECD and MBP-RAMP2 ECD [L106R]-CLR ECD fusion proteins were incubated for 1 hour on ice in the presence of CGRP(27-37)$NH_2$[N31D,S34P,K35F] or AM(25-52)$NH_2$ (1:1.3 protein:peptide molar ratio), respectively, in 10 mM Tris-HCl, pH 7.5, 50 mM NaCl, 1 mM EDTA, 1 mM maltose and spin concentrated to 30 mg/ml for crystallization. Crystals were grown by the hanging drop vapor diffusion method at 20° C. with a reservoir solution of 22% PEG3350, 8% Tacsimate (Hampton Research), pH 6.0 for the CGRP receptor complex or 19% PEG3350, 0.1 M Tris-HCl, pH 8.3, 225 mM sodium acetate, and 20% ethylene glycol for the $AM_1$ receptor complex. Microseeding was used to obtain the best CGRP receptor complex crystals for data collection. CGRP receptor complex crystals were cryoprotected by dialysis to mother liquor solution containing 12% PEG400; $AM_1$ receptor complex crystals were suitably cryoprotected in their growth condition. Crystals were flash frozen in liquid nitrogen and diffraction data were collected remotely at beamline 21-ID-G ($\lambda$=0.97857 Å) of the Advanced Photon Source (Argonne, Ill.). Data from single crystals were indexed, integrated, and scaled with HKL2000 v. 705b (Otwinowski and Minor, (1997). Processing of X-ray diffraction data collected in oscillation mode. In *Methods in Enzymology*, C. W. J. Carter, and R. M. Sweet, eds. (New York: Academic Press), pp. 307-326) and further processed/analyzed with the CCP4 suite v.6.4.0 (Winn et al., *Acta Crystallogr D Biol Crystallogr* (2011) 67:235-242) in preparation for molecular replacement (MR). The structures were solved with Phaser v. 2.5.6 (McCoy et al., *J Appl Crystallogr* (2007) 40:658-674) using an MBP search model with maltose removed (PDB 3C4M) followed by ligand-free CLR:RAMP1 ECD (PDB 3N7S) or CLR:RAMP2 ECD heterodimer search models (PDB 3AQF). The MR solutions were rigid body refined with REFMACS v. 5.8.0073 (Murshudov et al., *Acta Crystallogr D Biol Crystallogr* (1997) 53:240-255) treating MBP, CLR, and RAMP1 or RAMP2 as separate rigid bodies. At this stage $2mF_o-DF_c$ and $mF_o-DF_c$ electron density maps clearly showed bound maltose and CGRPmut or AM peptide. The models were completed by iterative rounds of manual rebuilding in COOT (Emsley et al., *Acta Crystallogr D Biol Crystallogr* (2010) 66:486-501) and TLS and restrained refinement with REFMACS. NCS restraints were applied to the three molecules in the ASU of the CGRP receptor complex structure with the restraints relaxed for areas where the molecules differed. Structure analysis used PyMol (Schrodinger) and programs in the CCP4 suite and figures were prepared with PyMol. Structural superpositions were performed with the PyMol align command (for Ca atoms) utilizing outlier rejection.

Homology Modeling. Homology models of RAMP3 were generated using Modeller 9v12 (Sali and Blundell, *J Mol Biol* (1993) 234:779-815). CGRPmut-bound CLR:RAMP1 and AM-bound CLR:RAMP2 template structures were used either singularly or in combination to generate the models. 6000 models were generated, refined using Rosetta 3.5 (Rohl et al., *Methods Enzymol* (2004) 383:66-93) and ranked using the OPUS_PSP scoring function (Lu et al., *J Mol Biol* (2008) 376, 288-301). The 600 best scoring structures were then clustered into 0.1 nm bins using the g cluster function as implemented in Gromacs (Pronk et al., *Bioinformatics* (2013) 29:845-854). The best scoring structure from the largest, best scoring cluster was then selected.

Cell-based assays. Transfection of COS-7 cells, cAMP assay, ELISA for cell surface expression, and data analysis were as previously described (Barwell et al., *Peptides* (2010) 31:170-176; Watkins et al., *Br J Pharmacol* (2014) 171:772-788).

Accession Numbers: Coordinates and structure factors were deposited in the RCSB Protein Data Bank with codes 4RWF and 4RWG for the AM:CLR:RAMP2 and CGRPmut:CLR:RAMP1 complexes, respectively.

Results

FIG. 1 depicts in (A) binding of a CGRP C-terminal peptide, CGRP(8-37)$NH_2$, and two variant AM C-terminal peptides (AM(37-52)$NH_2$[Q50W] and AM(37-52)$NH_2$[S45W,Q50W]) to purified CGRP receptor extracellular domain complex (CLR:RAMP1). FIG. 1 depicts in (B) binding of an AM C-terminal peptide, AM(37-52)$NH_2$, and the two variant AM C-terminal peptides to purified $AM_1$ receptor extracellular domain complex (CLR:RAMP2). The ability of the indicated peptides to displace a Biotin-CGRP probe (50 nM) from purified MBP-RAMP1 ECD-$(GS)_5$-CTR ECD-$H_6$ fusion protein (5 nM) or a Biotin-AM probe (25 nM) from purified MBP-RAMP2 ECD [L106R]-$(GS)_5$-CTR ECD-$H_6$ fusion protein (5 nM) was assessed by AlphaLISA® luminescent peptide binding assay (Perkin-Elmer, Waltham, Mass.). The probes were as described in Moad and Pioszak (*Protein Sci.* (2013) 22:1775-85). The reactions were incubated for 5 hours at room temperature to reach equilibrium, and the luminescence was measured in white 384-well plates using a BMG LABTECH's POLARstar® Omega plate reader (Ortenberg, Germany). The reaction buffer was 50 mM MOPS, pH 7.4, 150 mM NaCl, 7 mg/ml fatty acid-free BSA, and the streptavidin-coated donor beads and MBP-antibody coated acceptor beads were at 15 µg/ml each. $IC_{50}$ values were calculated using nonlinear regression fitting of the competition curves to a three-parameter, one-site competitive binding equation in GraphPad Prism 5.0 (GraphPad Software, San Diego Calif.).

FIG. 2 depicts binding of (A) AM-based peptide AM(37-52)$NH_2$; (B) variant peptides AM(37-52)$NH_2$[S45W, Q50W], AM(37-52)$NH_2$[Q50F], and AM(37-52)$NH_2$[Q50W]; (C) variant peptides AM(37-52)$NH_2$[D39K], AM(37-52)$NH_2$[K46L, Q50W], and AM(37-52)$NH_2$[K46L, Q50W, Y52F]; (D) variant peptides AM(37-52)$NH_2$[D39F, K46L, Q50W], AM(37-52)$NH_2$[D39F, K46L, Q50W, Y52F], and AM(37-52)$NH_2$[S45W, K46L, Q50W, Y52F]; (E) variant peptides AM(37-52)$NH_2$[S45W, K46M, Q50W, Y52F], and AM(37-52)$NH_2$[S45W, K46W, Q50W, Y52F]; (F) variant peptides AM(37-52)$NH_2$[S45T, K46W, Q50W], AM(37-52)$NH_2$[S45T, K46L, Q50W], and AM(37-52)$NH_2$[S45W, K46L, S48G, Q50W, Y52F]; (G) variant peptide AM(37-52)$NH_2$[S45W, K46L, I47M, Q50W, Y52F]; (H) variant peptides AM(37-52)$NH_2$[S45R, K46W, Q50W], and AM(37-52)$NH_2$[S45R, K46L, Q50W]; (I) variant peptides AM(37-52)$NH_2$[S45R, K46W, S48G, Q50W], AM(37-52)$NH_2$[S45R, K46L, S48G, Q50W], and AM(37-52)$NH_2$[S45R, K46W, I47L, S48G, Q50W]; and (J) variant peptides AM(37-52)$NH_2$[D39W, Q50W], and AM(37-52)$NH_2$[D37V, S45W, K46L, Q50W, Y52F], to the purified CGRP receptor extracellular domain complex (CLR:RAMP1). The ability of the indicated peptides to displace a FITC-Ahx-AM(37-52)$NH_2$ [S45W, Q50W] probe (7 nM) from purified MBP-RAMP1 ECD-$(GS)_5$-CLR ECD-$H_6$ fusion protein (15 nM) was assessed by fluorescence polarization (anisotropy).

The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 50 mM HEPES, pH 7.5, 150 mM NaCl, 0.5 mg/ml fatty acid-free BSA, 0.5 mM EDTA, 0.5 mM maltose. $K_I$ values were calculated using nonlinear regression fitting of the competition curves to the exact analytical equations of Roehrl et al. (*Biochemistry* (2004) 43:16056-66) using GraphPad Prism 5.0 (GraphPad Software, San Diego Calif.).

FIG. 3 depicts binding of (A) AM-based peptide AM(37-52)NH$_2$, and variant peptide AM(37-52)NH$_2$[S45W, Q50W]; (B) AM-based peptide AM(37-52)NH$_2$, variant peptide AM(37-52)NH$_2$[Q50F], and variant peptide AM(37-52)NH$_2$[Q50W]; (C) variant peptides AM(37-52)NH$_2$[K46L], AM(37-52)NH$_2$[K46M], and AM(37-52)NH$_2$[D39F]; (D) variant peptides AM(37-52)NH$_2$[D39F, K46L, Q50W], AM(37-52)NH$_2$[D39F, K46L, Q50W, Y52F], and AM(37-52)NH$_2$[S45W, K46L, Q50W, Y52F]; (E) variant peptides AM(37-52)NH$_2$[[D39K], AM(37-52)NH$_2$[K46L, Q50W], and AM(37-52)NH$_2$[K46L, Q50W, Y52F]; (F) variant peptides AM(37-52)NH$_2$[S45W, K46M, Q50W, Y52F], and AM(37-52)NH$_2$[S45W, K46W, Q50W, Y52F]; (G) variant peptides AM(37-52)NH$_2$[S45T, K46W, Q50W], AM(37-52)NH$_2$[S45T, K46L, Q50W], and AM(37-52)NH$_2$[S45W, K46L, S48G, Q50W, Y52F]; (H) variant peptide AM(37-52)NH$_2$[S45W, K46L, I47M, Q50W, Y52F]; (I) variant peptides AM(37-52)NH$_2$[S45R, K46W, Q50W], and AM(37-52)NH$_2$[S45R, K46L, Q50W]; (J) variant peptides AM(37-52)NH$_2$[S45R, K46W, S48G, Q50W], AM(37-52)NH$_2$[S45R, K46L, S48G, Q50W], and AM(37-52)NH$_2$[S45R, K46W, I47L, S48G, Q50W]; and (K) variant peptides AM(37-52)NH$_2$[D39W, Q50W], and AM(37-52)NH$_2$[D37V, S45W, K46L, Q50W, Y52F], to the purified AM$_1$ receptor extracellular domain complex. Single representative experiments conducted with duplicate samples are shown. Error bars are S.E.M. The ability of the indicated peptides to displace a FITC-Ahx-AM(37-52)NH$_2$[S45W, Q50W] probe (7 nM) from purified MBP-RAMP2 ECD [L106R]-(GS)$_5$-CLR ECD-H$_6$ fusion protein (110 nM) was assessed by fluorescence polarization (anisotropy). The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 50 mM HEPES, pH 7.5, 150 mM NaCl, 0.5 mg/ml fatty acid-free BSA, 0.5 mM EDTA, 0.5 mM maltose. $K_I$ values were calculated using nonlinear regression fitting of the competition curves to the exact analytical equations of Roehrl et al. (*Biochemistry* (2004) 43:16056-66) using GraphPad Prism 5.0 (GraphPad Software, San Diego Calif.).

FIG. 4 depicts binding of (A) CGRP-based peptide CGRP[8-37]NH$_2$; (B) variant peptides CGRP(27-37)NH$_2$[N31D, S34P, K35F], CGRP(27-37)NH$_2$[N31D, S34P, K35W], and CGRP(27-37)NH$_2$[N31D, S34P, K35F, A36S]; (C) variant peptides CGRP(27-37)NH$_2$[N31D, S34P, K35W, A36S], and CGRP(27-37)NH$_2$[N31D, S34P, K35W, A36S, F37Y]; (D) variant peptides CGRP(27-37)NH$_2$[N31D, V32T, S34P, K35W, A36G], and CGRP(27-37)NH$_2$[N31D, V32T, S34P, K35W, A36G, F37Y]; and (E) variant peptide CGRP(27-37)NH$_2$[N31D, V32T, S34P, K35W, A36S], to the purified CGRP receptor extracellular domain complex. Single representative experiments conducted with duplicate samples are shown. Error bars are S.E.M. The ability of the indicated peptides to displace a FITC-Ahx-AM(37-52)NH$_2$[S45W, Q50W] probe (7 nM) from purified MBP-RAMP1 ECD-(GS)$_5$-CLR ECD-H$_6$ fusion protein (15 nM) was assessed by fluorescence polarization (anisotropy). The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 50 mM HEPES, pH 7.5, 150 mM NaCl, 0.5 mg/ml fatty acid-free BSA, 0.5 mM EDTA, 0.5 mM maltose. $K_I$ values were calculated using nonlinear regression fitting of the competition curves to the exact analytical equations of Roehrl et al. (*Biochemistry* (2004) 43:16056-66) using GraphPad Prism 5.0 (GraphPad Software, San Diego Calif.).

FIG. 5 depicts binding of (A) CGRP-based peptide CGRP (11-37)NH$_2$; (B) variant peptides CGRP(27-37)NH$_2$[N31D, S34P, K35F], CGRP(27-37)NH$_2$[N31D, S34P, K35W], and CGRP(27-37)NH$_2$[N31D, S34P, K35F, A36S]; (C) variant peptides CGRP(27-37)NH$_2$[N31D, S34P, K35W, A36S], and CGRP(27-37)NH$_2$[N31D, S34P, K35W, A36S, F37Y]; (D) variant peptides CGRP(27-37)NH$_2$[N31D, V32T, S34P, K35W, A36G], and CGRP(27-37)NH$_2$[N31D, V32T, S34P, K35W, A36G, F37Y]; and (E) variant peptide CGRP(27-37)NH$_2$[N31D, V32T, S34P, K35W, A36S], to the purified AM$_1$ receptor extracellular domain complex. Single representative experiments conducted with duplicate samples are shown. Error bars are S.E.M. The ability of the indicated peptides to displace a FITC-Ahx-AM(37-52)NH$_2$[S45W, Q50W] probe (7 nM) from purified MBP-RAMP2 ECD [L106R]-(GS)$_5$-CLR ECD-H$_6$ fusion protein (110 nM) was assessed by fluorescence polarization (anisotropy). The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 50 mM HEPES, pH 7.5, 150 mM NaCl, 0.5 mg/ml fatty acid-free BSA, 0.5 mM EDTA, 0.5 mM maltose. $K_I$ values were calculated using nonlinear regression fitting of the competition curves to the exact analytical equations of Roehrl et al. (*Biochemistry* (2004) 43:16056-66) using GraphPad Prism 5.0 (GraphPad Software, San Diego Calif.).

Figure 6:
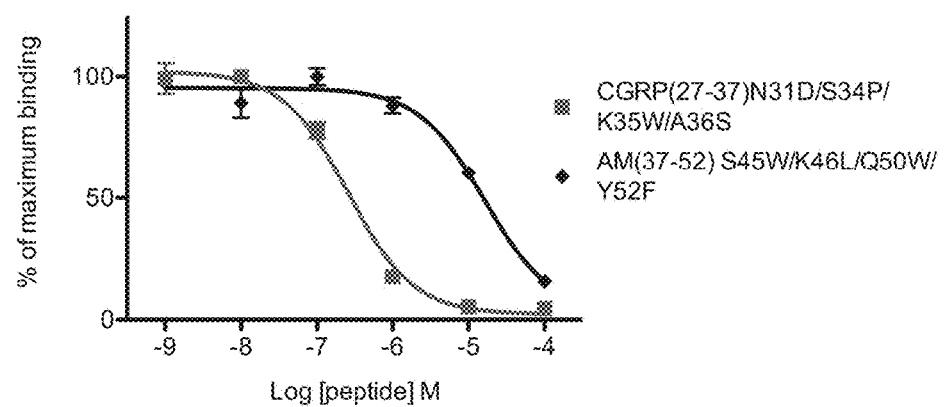
FIG. 6 depicts binding of CGRP variant peptide CGRP(27-37)NH$_2$[N31D, S34P, K35W, A36S] and AM variant peptide AM(37-52)NH$_2$[S45W, K46L, Q50W, Y52F], to purified AMY$_1$ receptor extracellular domain complex. A single representative experiment conducted with duplicate samples is shown. Error bars are S.E.M.

FIG. 6 depicts binding of CGRP variant peptide CGRP (27-37)NH$_2$ [N31D, S34P, K35W, A36S] and AM variant peptide AM(37-52)NH$_2$ [S45W, K46L, QSOW, Y52F], to purified AMY$_1$ receptor extracellular domain complex. A single representative experiment conducted with duplicate samples is shown. Error bars are S.E.M. The ability of the indicated peptides to displace a Biotin-AC413 probe (100 nM) from purified MBP-RAMP1 ECD-(GS)$_5$-CTR ECD-H$_6$ fusion protein (200 nM) was assessed by AlphaLISA® luminescent peptide binding assay (Perkin-Elmer, Waltham, Mass.) as described in Lee et al. (*J Biol. Chem* (2016) 291:8686-8700). The reactions were incubated for 5 hours at room temperature to reach equilibrium, and the luminescence was measured in white 384-well plates using a BMG LABTECH's POLARstar® Omega plate reader (Ortenberg, Germany). The reaction buffer was 50 mM MOPS, pH 7.4, 150 mM NaCl, 7 mg/ml fatty acid-free BSA and the streptavidin-coated donor beads and MBP-antibody coated acceptor beads were at 15 µg/ml each. IC$_{50}$ values were calculated using nonlinear regression fitting of the competition curves to a three-parameter, one-site competitive binding equation in GraphPad Prism 5.0 (GraphPad Software, San Diego Calif.). The IC$_{50}$ values for CGRP (27-37)NH$_2$[N31D, S34P, K35W, A36S] and AM (37-52)NH$_2$[S45W, K46L, Q50W, Y52F] were 260 nM and 16 µM, respectively.

FIG. 7 depicts antagonism of cAMP signaling at full-length (A) CGRP (RAMP1:CLR) and (B) AM$_1$ (RAMP2:CLR) receptor complexes transiently expressed in COS-7 cells by the variant peptide AM(37-52)NH$_2$[S45W, K46L, Q50W, Y52F]. A single representative experiment conducted with duplicate samples is shown. Error bars are S.E.M. The experiments were performed as described in Lee et al. (*J Biol. Chem* (2016) 291:8686-8700). (A) depicts antagonism of CGRP-activated cAMP signaling at the CGRP receptor. The pA$_2$ value calculated by fitting the curves to a Gaddum/Schild EC$_{50}$ shift equation with Hill and Schild slopes constrained to 1 in GraphPad Prism 5.0 was 7.98. (B) depicts antagonism of AM-activated cAMP signaling at the AM$_1$ receptor.

FIG. 8 depicts binding of AM-based PS-SPCL library mixtures to purified CGRP (A, C, E) and AM$_1$ (B, D, F) receptor extracellular domain complexes. One of 5 positions of the 16 positions in variant AM(37-52)NH$_2$[Q50W] was optimized for each mixture. In (A, B) position 45 was optimized, in (C, D) position 46 was optimized, in (E, F) position 47 was optimized, in (G, H) position 48 was optimized, and in (I, J) position 52 was optimized. The ability of the indicated mixtures to displace a FITC-Ahx-AM(37-52)NH$_2$ [S45W, Q50W] probe (7 nM) from purified MBP-RAMP1 ECD-(GS)$_5$-CLR ECD-H$_6$ fusion protein (15 nM) or MBP-RAMP2 ECD [L106R]-(GS)$_5$-CLR ECD-H$_6$ fusion protein (110 nM) was assessed by fluorescence polarization (anisotropy). The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 100 mM HEPES, pH 7.5, 150 mM NaCl, 0.5 mg/ml fatty acid-free BSA, 0.5 mM EDTA, 0.5 mM maltose. The final library mixture concentrations were 0.05 mg/ml for the CGRP receptor ECD complex and 0.5 mg/ml for the AM$_1$ receptor ECD complex.

FIG. 9 depicts binding of CGRP-based PS-SPCL library mixtures to purified CGRP receptor extracellular domain complexes. One of 5 positions of the 11 positions in variant CGRP(27-37)NH$_2$[S34P, K35W] was optimized for each mixture. In (A) position 31 was optimized, in (B) position 32 was optimized, in (C) position 33 optimized, in (D) position 36 optimized, and in (E) position 37 optimized. Single experiments conducted with duplicate samples are shown. Error bars are S.E.M. (−) indicates no competitor control. The ability of the indicated mixtures to displace a FITC-Ahx-AM(37-52)NH$_2$ [S45W, Q50W] probe (7 nM) from purified MBP-RAMP1 ECD-(GS)$_5$-CLR ECD-H$_6$ fusion protein (15 nM) was assessed by fluorescence polarization (anisotropy). The reactions were incubated for 2 hours at room temperature to reach equilibrium, and the anisotropy was measured in black half-area 96-well plates using a BMG LABTECH's POLARstar® Omega plate reader (Ortenberg, Germany). The reaction buffer was 100 mM HEPES, pH 7.5, 150 mM NaCl, 0.5 mg/ml fatty acid-free BSA, 0.5 mM EDTA, 0.5 mM maltose. The final library mixture concentrations were 0.11 mg/ml. The peptide mixture for Q at position 37 was problematic for unknown reasons and was therefore omitted.

Discussion

Tethered RAMP1 ECD- and RAMP2 ECD-CLR ECD fusion proteins were engineered to enhance complex stability (Moad and Pioszak. *Protein Sci*. (2013) 22:1775-85). The fusions selectively bound their respective peptides with μM affinities. Structures of RAMP1-CLR ECD in complex bound with a high-affinity antagonist CGRP analog ("CGRPmut"—SEQ ID NO:35), and RAMP2-CLR ECD bound to an antagonist AM fragment, revealing that the peptides occupy a shared binding site on CLR with largely unstructured conformations characterized by a β-turn near their C-terminus. AM contains a single α-helical turn that is absent in CGRPmut. These conformations contrast the continuous α-helices formed by other ECD-bound class B GPCR peptide ligands. Two key areas of the CLR peptide-binding site are a hydrophobic patch and a pocket that is augmented by the RAMP. Prior to the β-turn, the peptides contact the patch, and after the β-turn, their C-terminal residue occupies the pocket. CGRPmut F37 makes hydrophobic contact with RAMP1 W84, and AM Y52 forms a key hydrogen bond with RAMP2 E101. The structures and a RAMP3 homology model (not shown) explain how these RAMP-peptide contacts affect selectivity. RAMP2 E101 and RAMP3 E74 favor AM by H-bonding with Y52. RAMP1 W74 precludes this bond. RAMP1 W84 enables contact with CGRP F37, whereas the smaller F111 at the equivalent RAMP2 position precludes this contact, thereby disfavoring CGRP binding. RAMP3 W84 probably explains why CGRP is more potent at AM$_2$ than AM$_1$. RAMP-peptide contact clearly is important for ligand selectivity at CLR, but allostery may also play a role. Swapping the CGRP and AM C-terminal residues did not switch their receptor selectivity, which suggested that RAMP-peptide contact alone cannot explain selectivity. Subtle differences in CLR conformation in the two structures appear to be RAMP-dependent including different positions of CLR R119 and slightly different pocket shapes.

Development of AM and CGRP Variants with Enhanced Potency and Selectivity for the CGRP or AM Receptors.

Our recent crystal structures of the CGRPmut:RAMP1-CLR ECD and AM:RAMP2-CLR ECD complexes at resolutions of 2.5 and 1.8 Å, respectively, revealed the structural basis for peptide recognition and provided insights into how RAMPs determine ligand selectivity. In our crystal structure of peptide-bound RAMP1-CLR ECD, a high-affinity CGRP analog was used, because it yielded higher-quality crystals than CGRP. This analog, "CGRPmut" (SEQ ID NO:35), was developed by Rist et al. (*J Med Chem*. (1998) 41(1):117-23) using systematic mutagenesis in which the C-terminal antagonist fragment (27-37) was scanned with several amino acids. The results revealed the basis for the enhanced affinity. The N31D substitution does not appear to provide affinity enhancement, but it probably increases peptide solubility. The S34P substitution promotes β-turn formation equivalent to AM P49, and K35F increases hydrophobic contact to CLR loop4 (FIG. 1A). It was hypothesized that substitution of AM Q50 (equivalent to CGRP K35) with F or W would similarly enhance affinity. Using the molecular graphics software Pymol (Schrodinger), in silico mutagenesis was performed to model substitutions at AM Q50 and other positions. The modeling suggested that Q50W would contact CLR S117 and R119 in loop4 and that the addition of S45W in a double mutant would allow stacking of the Trp residues, which may stabilize the β-turn. Custom synthesized and HPLC-purified AM(37-52) antagonist peptides containing the Q50W and S45W/Q50W mutations were synthesized and tested for binding to the CGRP and AM$_1$ receptor ECD complexes using an AlphaLISA® luminescent proximity assay (Perkin-Elmer, Waltham, Mass.) with purified tethered MBP-RAMP1 ECD-CLR ECD and MBP-RAMP2 ECD-CLR ECD fusion proteins as described. All data used purified MBP-RAMP ECD-CLR/CTR ECD fusions; "MBP" is often omitted hereafter. Human peptides and receptors were used unless otherwise noted, and all peptides were C-terminally amidated.

In competition assays, the AM(37-52)NH$_2$[Q50W] single mutant had ~100-fold increased affinity for RAMP2-CLR ECD and significantly enhanced affinity for RAMP1-CLR ECD. The S45W/Q50W double mutant did not appear to further enhance binding to RAMP2-CLR ECD, but it enhanced binding to RAMP1-CLR ECD such that it was non-selective with apparent nM affinity. AlphaLISA®/AlphaScreen® can detect weak molecular interactions (μM $K_d$) using nM concentrations of binding partners in part due to multivalency resulting from the two-bead assay format, but this avidity effect and other peculiarities of the technology complicate determination of accurate binding affinities. The IC$_{50}$ values in competition AlphaLISA®/AlphaScreen® assays often provide reasonable estimates of the true affinities, but a more rigorous quantitative binding assay was desired to enable determination of accurate peptide affinities.

Robust FP Assay for Determining Peptide Affinities for Purified Receptor ECD Complexes.

A fluorescence polarization/anisotropy (FP) peptide-binding assay was developed using N-terminally FITC-labeled AM(37-52) S45W/Q50W as the probe, hereafter "FITC-AM W/W." The probe was custom synthesized and HPLC-purified by RS Synthesis. The large size difference between the MBP-RAMP ECD-CLR ECD fusion proteins (~65 kDa) and the probe (~2.5 kDa) ensures a significant anisotropy difference between bound and free states of the probe. The assay was extensively optimized, and several controls confirmed its validity (data not shown). $K_d$ values for the probe at each of the tethered ECD fusion proteins were determined in equilibrium saturation binding experiments (data not shown), and $K_I$ values were determined for unlabeled peptides in equilibrium competition experiments (Table 1; FIGS. 2-5). The data were analyzed according to exact analytical equations using non-linear regression curve fitting in GraphPad Prism 5.0 (GraphPad Software) via user-defined equations. CGRP(8-37)NH$_2$ peptide bound RAMP1-CLR ECD with a 57.5 μM $K_I$ in the FP assay, which is in excellent agreement with the 57 μM $K_d$ obtained by ITC. AM(37-52)NH$_2$ peptide bound RAMP2-CLR ECD with a 20.4 μM $K_I$, which is in good agreement with AlphaLISA® or AlphaScreen® competition assays (IC$_{50}$ 5-15 μM). The FP assay indicated that AM Q50W enhanced affinity more than Q50F and confirmed non-selective nM affinity of the S45W/Q50W double mutant. CGRPmut bound RAMP1-CLR ECD with a $K_I$ of 36 nM, which is close to the 29 nM IC$_{50}$ reported for its binding to membranes of SK-N-MC cells, which express the CGRP receptor.

TABLE 1

Affinity of variant peptides for purified ECD complexes of the CGRP and AM$_1$ receptors as determined by fluorescence polarization assay

| Peptide | RAMP1-CLR ECD (CGRP) pK$_I$*; K$_I$ (nM) | RAMP2-CLR ECD (AM$_1$) pK$_I$; K$_I$ (nM) | Receptor Selectivity |
|---|---|---|---|
| AM(37-52)NH$_2$ scaffold | | | |
| WT | <4; >100,000 | 4.69 ± 0.05; 20,400 | AM$_1$ over CGRP |
| Q50F | 4.98 ± 0.03; 10,500 | 5.67 ± 0.06; 2140 | 5-fold for AM$_1$ |
| Q50W | 6.30 ± 0.04; 501 | 6.50 ± 0.06; 316 | Non-selective |
| K46L | No binding | No binding | |
| K46M | No binding | No binding | |
| D39F | No binding | No binding | |
| D39K | No binding | 5.22 ± 0.05; 6100 | AM$_1$ |
| S45W/Q50W | 7.35 ± 0.06; 44.7 | 7.09 ± 0.04; 81.3 | Non-selective |
| K46L/Q50W | 7.15 ± 0.03; 70.8 | 5.78 ± 0.02; 1660 | 23-fold for CGRP |
| K46L/Q50W/Y52F | 7.50 ± 0.08; 31.6 | 4.05 ± 0.17; 89,100 | 2820-fold for CGRP |
| D39F/K46L/Q50W | 7.10 ± 0.06; 82.2 | 5.74 ± 0.07; 1833 | 22-fold for CGRP |
| D39F/K46L/Q50W/Y52F | 7.61 ± 0.03; 25.0 | 4.55 ± 0.08; 30,333 | 1213-fold for CGRP |
| S45W/K46L/Q50W/Y52F | 8.72 ± 0.11; 1.91 | 5.39 ± 0.05; 4070 | 2131-fold for CGRP |
| S45W/K46M/Q50W/Y52F | 8.10 ± 0.13; 7.94 | 5.11 ± 0.04; 7760 | 977-fold for CGRP |
| S45W/K46W/Q50W/Y52F | 7.62 ± 0.04; 24.0 | 4.78 ± 0.03; 16,600 | 692-fold for CGRP |
| S45T/K46W/Q50W | 6.36; 439.5 | 4.90; 12,500 | 28-fold for CGRP |
| S45T/K46L/Q50W | 7.18; 65.6 | 5.80; 1570 | 24-fold for CGRP |
| S45W/K46L/S48G/Q50W/Y52F | ND# | 5.90; 1250 | ND |
| S45W/K46L/I47M/Q50W/Y52F CGRP | 9.11; 0.78 | No binding | CGRP (very selective) |
| CGRP(11-37)NH$_2$ | 4.24 ± 0.10; 57,500 | No binding | CGRP |
| CGRP(27-37)NH$_2$ scaffold | | | |
| CGRPmut [N31D/S34P/K35F]$^&$ | 7.44 ± 0.11; 36.3 | No binding | CGRP |
| N31D/S34P/K35W | 8.09 ± 0.03; 8.13 | No binding | CGRP |
| N31D/S34P/K35F/A36S | 8.53 ± 0.08; 2.95 | <5; >10,000; | CGRP over AM$_1$ |

TABLE 1-continued

Affinity of variant peptides for purified ECD complexes of the CGRP and AM$_1$ receptors as determined by fluorescence polarization assay

| Peptide | RAMP1-CLR ECD (CGRP) pK$_I$*; K$_I$ (nM) | RAMP2-CLR ECD (AM$_1$) pK$_I$; K$_I$ (nM) | Receptor Selectivity |
|---|---|---|---|
| N31D/S34P/K35W/A36S | 8.88 ± 0.10; 1.32 | 5.61 ± 0.07; 2450 | 1856-fold for CGRP |
| N31D/S34P/K35W/A36S/F37Y | 8.88 ± 0.25; 1.32 | 6.49 ± 0.09; 324 | 245-fold for CGRP |
| N31D/V32T/S34P/K35W/A36G | 8.16; 6.85 | No binding | CGRP |
| N31D/V32T/S34P/K35W/A36G/F37Y | 7.75; 17.6 | 4.84; 14,454 | 821-fold for CGRP |
| N31D/V32T/S34P/K35W/A36S | >9; <1.0## | 5.56; 2754 | ≥2754-fold for CGRP |

*pK$_I$ values are reported as mean ± S.E.M of at least 3 independent experiments.
ND; not determinable.
&high-affinity antagonist identified in Rist, et al., J Med Chem (1998).
K$_I$ in the pM range beyond what can be reliably measured with our FP assay.

Design and Characterization of AM and CGRP Antagonist Variants with Further Enhanced Potency and Selectivity.

Superposition of the CGRPmut- and AM-bound structures reveals slight differences in the shapes of the pocket occupied by the peptide C-terminal residue. As compared to RAMP1, RAMP2 causes a slight twist of CLR α1 relative to the remainder of the ECD that appears to propagate to CLR loop2. The subtle differences in loop2 appear to displace the AM Y52 phenyl ring relative to that of CGRPmut F37. It was hypothesized that this allosteric effect of RAMPS contributes to selectivity. The single α-helical turn in AM allows the aliphatic portion of the K46 side chain to contact the CLR "Trp shelf" at the base of the pocket and intramolecularly pack against the AM Y52 phenyl ring. The AM K46 ε-amino group is close to RAMP2 E105, and E101 and appears to provide H-bond and/or ionic interactions with these residues; however, mutagenesis suggested that these interactions are insignificant compared to the K46 hydrophobic contacts. Several AM variants with K46L or K46M combined with the previously identified mutations and/or Y52F to remove the key H-bond between AM Y52 and RAMP2 E101 were purchased and tested in the FP assay (Table 1; FIGS. 2-3). K46W was also tested even though modeling suggested a Trp might pack against Y52 without displacing it towards loop2. The results supported the allostery hypothesis, as several potent AM(37-52)NH$_2$ variants selective for the CGRP receptor were identified. AM(37-52) NH$_2$ [S45W/K46L/Q50W/Y52F] had an affinity of ~2 nM for RAMP1-CLR ECD and was >2000-fold selective.

H-bond with the D31 backbone carbonyl to stablize the β-turn. These substitutions generated CGRP(27-37)NH$_2$ [N31D/S34P/K35W/A36S] with ~1 nM affinity for RAMP1-CLR ECD (Table 1; FIGS. 4-5). Inclusion of F37Y yielded CGRP(27-37)NH$_2$[N31D/S34P/K35W/A36S/F37Y], which gained significant affinity for RAMP2-CLR ECD (324 nM K$_I$), but still preferred RAMP1-CLR ECD. These results indicated that CGRP and AM can be altered to gain significant affinity for the opposite receptor.

ECD or ECD complexes were purified for five of the seven receptors arising from CLR/CTR and RAMPS: CGRP, AM$_1$, CTR, AMY$_1$, and AMY$_2$ (Table 2). Expression and purification of tethered fusions with RAMP3 ECD has thus far proven difficult. MBP-CTR ECD, MBP-RAMP1-CTR ECD, and MBP-RAMP2-CTR ECD were expressed, purified, and characterized. RAMP1-CLR and RAMP2-CLR ECD were produced in E. coli, but HEK293T cells were used to produce the CTR-based proteins because N-glycosylation of CTR may influence its ligand binding. CTR ECD, RAMP1-CTR ECD, and RAMP2-CTR ECD reproduced the ligand selectivity of the intact receptors; tethering RAMP1 to CTR enhanced rAmy and CGRP affinity. Notably, CGRP(27-37)NH$_2$ [N31D/S34P/K35W/A36S] had significantly stronger affinity for RAMP1-CTR than AM(37-52)NH$_2$[S45W/K46L/Q50W/Y52F] (FIG. 6), which indicates that AM-based variants may be more promising as CGRP receptor antagonists for migraines because they are likely to be more selective against AMY$_1$ than CGRP-based variants.

TABLE 2

Summary of human receptors for CT family peptides

| Receptor (designation) | Composition | Peptide agonist potency |
|---|---|---|
| CGRP receptor (CGRP) | CLR + RAMP1 | CGRP > AM, AM2 > Amy |
| Adrenomedullin receptor (AM$_1$) | CLR + RAMP2 | AM > AM2 >> CGRP > Amy |
| Adrenomedullin receptor (AM$_2$) | CLR + RAMP3 | AM > AM2 > CGRP > Amy |
| Calcitonin receptor (CTR) | CTR alone | CT > Amy, CGRP > AM, AM2 |
| Amylin receptor (AMY$_1$) | CTR + RAMP1 | Amy ≈ CT ≈ CGRP > AM2 >> AM |
| Amylin receptor (AMY$_2$) | CTR + RAMP2 | Increased Amy affinity, but poorly defined |
| Amylin receptor (AMY$_3$) | CTR + RAMP3 | Amy > CT > CGRP > AM, AM2 |

CGRP(27-37)NH$_2$ variants with affinity greater than "CGRPmut" (SEQ ID NO:35) were generated by introducing W at position 35 to provide more hydrophobic contact to CLR loop4 and/or S at position 36 to form an intramolecular This work with purified tethered ECD fusion proteins has indicated that they accurately recapitulate the ECD complexes as they exist in the intact receptors, but it is nonetheless useful to characterize the engineered variants at intact receptors in cells. COS-7 cells do not express CLR/CTR or RAMPs and thus provide a clean background for pharmacological studies of the heterologously expressed receptors. The ability of AM(37-52)NH$_2$[S45W/K46L/Q50W/Y52F] to antagonize the CGRP and AM$_1$ receptors transiently expressed in COS-7 cells was assessed. Forty-eight hours after transfection, the cells were pre-incubated for 30 minutes in the absence or presence of 500 nM AM(37-52)NH$_2$ [S45W/K46L/Q50W/Y52F], and then stimulated for 15 minutes with increasing concentrations of agonist peptide in the absence or presence of 500 nM antagonist. The cells were lysed, and cAMP was quantitated using a LANCE TR-FRET cAMP kit (Perkin-Elmer Waltham, Mass.). The concentration-response curves were fit by non-linear regression using GraphPad Prism 5.0 to a Gaddum/Schild EC$_{50}$ shift equation with Hill and Schild slopes constrained to 1 to determine pA$_2$ values (a measure of antagonist potency). AM(37-52)NH$_2$[S45W/K46L/Q50W/Y52F] antagonized the CGRP receptor with a pA$_2$ of ~8 and did not antagonize the AM$_1$ receptor (FIGS. 7A,B). This indicates that AM(37-52)NH$_2$[S45W/K46L/Q50W/Y52F] functions selectively at the intact CGRP receptor in cells and suggests an affinity of ~10 nM for the intact receptor, which is close to the ~2 nM K$_I$ for the ECD complex (Table 1).

Identification of Potent and Selective Peptides for the CGRP and AM Receptors Using Synthetic Peptide Combinatorial Libraries.

Synthetic peptide combinatorial libraries (SPCL) provide an alternative to rational design that is a less-biased approach to identify optimized peptides from mixtures of thousands to millions of variants. The positional scanning-SPCL (PS-SPCL) method can identify optimal amino acids at a given position considering all possible combinations at several other positions. This approach has been used to develop potent peptides selective for opioid receptors. It was hypothesized that the FP assay could be leveraged to screen AM- and CGRP-based PS-SPCLs for binding to RAMP1-CLR and RAMP2-CLR ECD to identify potent and selective antagonist variants that might have been missed by the rational approach.

PS-SPCL for the AM and CGRP Antagonist Fragments and FP-Based Screening.

The number of positions that can be randomized in the PS-SPCL approach depends on various factors, such as (but not limited to) solubility of the peptide mixtures, concentration of mixtures needed to see an effect in the FP assay, etc. Taking these into consideration, 5 of the 16 positions in AM(37-52)NH$_2$[Q50W] (according to SEQ ID NO:53) and 5 of the 11 positions in CGRP(27-37)NH$_2$[S34P, K35W] (according to SEQ ID NO:54) were optimized. Although including AM Q50W and CGRP K35W identified by rational design introduces bias, it was predicted that the non-selective affinity increases conferred by these mutations would permit lower peptide concentrations to be used in case of solubility problems. AM positions S45, K46, I47, S48, and Y52 were chosen as positions for randomization based on structural considerations. CGRP positions N31, V32, G33, A36, and F37 were chosen for optimization also based on structural considerations. Each complete PS-SPCL library includes 5 "positional libraries" corresponding to the 5 positions to be optimized. Each positional library contains 19 peptide mixtures, wherein that position is defined with one of 19 natural amino acids (no cysteine), and the other 4 positions are randomized with an equimolar mixture of the 19 amino acids. The 5 AM-based positional libraries were based on SEQ ID NO:53, wherein positions 45, 46, 47, 48, and 52 were defined in consecutive sequences, and the other four positions in each sequence were randomized. The 5 CGRP-based positional libraries were based on SEQ ID NO:54, wherein positions 31, 32, 33, 36, and 37 were defined in consecutive sequences, and the other four positions in each sequence were randomized. The total number of peptide mixtures for each library is 95 (5*19), and each of the mixtures contains 130,321 unique variant peptides ($19^4$). These custom-synthesized PS-SPCLs were purchased from RS Synthesis (Louisville, Ky.). Individual lyophilized mixtures were reconstituted in 10% DMSO at 10 mg/ml for the AM library or in 25% DMSO at 7.5 mg/ml for the CGRP library. The positional libraries were screened in the FP competition assay with each AM library mixture at 0.05 mg/ml for RAMP1-CLR ECD or 0.5 mg/ml for RAMP2-CLR ECD and each CGRP library mixture at 0.11 mg/ml for RAMP1-CLR ECD. The CGRP library was also screened at RAMP2-CLR ECD, but no significant binding was observed (data not shown). The results of the entire screen for the AM library at both the CGRP and AM$_1$ receptor ECD complexes are shown in FIG. 8, and the results of the entire screen for the CGRP library at the CGRP receptor ECD complex is shown in FIG. 9. These experiments validated the PS-SPCL approach, because W at position 45 and L, W, or M at position 46 of AM were identified as conferring the strongest binding to RAMP1-CLR ECD, in agreement with the rational design results. Encouragingly, the results indicated that variants were missed by rational design. For example, R at position 45 of AM conferred strong binding to RAMP2-CLR ECD but did not enhance binding to RAMP1-CLR ECD. The screen results identify ideal residues at each position that confer strong affinity when in combination with certain residues at the other positions. As more than one good residue was sometimes identified at a given position, there is some ambiguity in interpreting the screen. Nonetheless, by modeling various peptide sequence combinations identified in the screens, additional designs of interest were identified. Synthetic peptides corresponding to these designs were ordered and tested in the FP assay for binding to each of the complexes. (FIGS. 2-5). This approach allowed the identification of AM(37-52)NH$_2$[S45W, K46L, I47M, Q50W, Y52F] as an extremely high affinity (K$_I$~780 pM) antagonist ligand for the CGRP receptor ECD complex with exquisite selectivity, as no binding to the AM$_1$ receptor ECD complex was detected (Table 1). CGRP(27-37)NH$_2$ [N31D, V32T, S34P, K35W, A36S] was similarly identified as an extremely high affinity CGRP receptor antagonist with affinity well into the pM range, such that its affinity could not be accurately determined by the FP assay (Table 1). This peptide was also significantly selective for the CGRP receptor.

Variants of AM and CGRP

The variant peptides of the present disclosure include, but are not limited to, variants of wild-type human adrenomedullin (AM) and variant fragments thereof, and variants of calcitonin gene-related peptides (α-CGRP and β-CGRP) and variant fragments thereof which bind to at least one of the CLR:RAMP1, CLR:RAMP2, and CLR:RAMP3 receptor complexes with an affinity characterized by a K$_I$ less than about 1 μM, for example under conditions described elsewhere herein. In certain embodiments, the variants have higher receptor affinity and increased selectivity than wild type AM and/or wild type α-CGRP, and/or wild type β-CGRP. The variants, in general, are C-terminally amidated. Any of the variant peptides disclosed herein can be used with a pharmaceutically-acceptable carrier in a composition, for example for use in treatment of the conditions and diseases described elsewhere herein.

In at least certain embodiments, amino acids 1-12 of AM can be deleted without affecting binding activity of the remaining AM fragment. In at least certain embodiments, approximately the N-terminal half of the 13-52 peptide fragment of SEQ ID NO:1 interacts with the receptor 7-transmembrane (7TM) domain and the C-terminal portion interacts with the receptor extracellular domain (ECD). The N-terminal portion (e.g., amino acids 13-21) causes activation of the receptor 7TM domain; thus the 13-52 peptide has agonistic activity. Antagonistic versions (which bind to one or more of the CLR:RAMP1-3 receptor complexes but which do not activate the receptor complex) can be generated by deleting the N-terminal portion comprising amino acids 13-21. Thus AM variants based on amino acids 22-52 of SEQ ID NO:1 or, for example, AM fragments consisting of amino acids 37-52 of AM (DKDNVAPRSKISPQGY— SEQ ID NO:4) and variants thereof, have an antagonistic effect on the corresponding CLR:RAMP receptor complex.

Any mutation in a C-terminal portion in AM that causes higher receptor affinity and/or selectivity in a shortened antagonist fragment will also give rise to an agonistic peptide with a higher affinity (and thereby higher potency) when incorporated into the full length AM peptide (SEQ ID NO:1) or into an agonistic fragment thereof (e.g., amino acids 13-52 of SEQ ID NO:1).

Similarly, any mutation in a C-terminal portion of CGRP that causes higher receptor affinity and/or selectivity in a shortened antagonist fragment (e.g., amino acids 8-37) will also give rise to an agonistic peptide with a higher affinity (and thereby higher potency) when incorporated into the full length CGRP peptide (37 amino acids) or into an agonistic fragment thereof (in CGRP peptides, the N terminal 1-7 amino acid portion activates the receptor 7TM domain; thus the 8-37 peptide is an antagonist). CGRP peptide fragment FVPTNVGSKAF-NH$_2$ (SEQ ID NO:34) is a C-terminal binding portion having antagonistic activity against the cognate receptor complex. FVPTDVGPFAF-NH$_2$ (SEQ ID NO: 35) is an antagonistic mutant of this peptide fragment, having high affinity for CGRP receptor (see Rist et al. (*J Med Chem*. (1998) 41(1):117-23)), but it also has higher affinity for the AM$_1$ receptor.

The embodiments of the present disclosure include, but are not limited to, variants and variant fragments of wild-type human adrenomedullin (AM) and/or calcitonin gene-related peptide (CGRP) peptide which have higher affinity than the wild type peptide for at least one of, two of, or all three of the AM$_1$, AM$_2$, and CGRP receptors, wherein higher affinity means at least 50-fold, at least 100-fold, at least 200-fold, at least 300-fold, at least 400-fold, at least 500-fold, at least 600-fold, at least 700-fold, at least 800-fold, at least 900-fold, at least 1000-fold, at least 1100-fold, at least 1200-fold, at least 1300-fold, at least 1400-fold, at least 1500-fold, at least 1600-fold, at least 1700-fold, at least 1800-fold, at least 1900-fold, at least 2000-fold, at least 2500-fold, at least 3000-fold, at least 3500-fold, at least 4000-fold, at least 4500-fold, at least 5000-fold, at least 5500-fold, at least 6000-fold, at least 6500-fold, at least 7000-fold, at least 7500-fold, at least 8000-fold, at least 8500-fold, at least 9000-fold, at least 9500-fold, at least 10000-fold, at least 15000-fold, or at least 20000-fold, or greater, affinity, for at least one of, two of, or all three of the AM$_1$, AM$_2$, and CGRP receptors. In certain embodiments, the variant peptides bind only to the ECD complex of CLR and the associated RAMP portion of the receptor (wherein the variant is a receptor complex antagonist), or to both the ECD complex and the 7TM portion of CLR (wherein the variant peptide is a receptor complex agonist). The variant peptides of the present disclosure may have affinity K$_i$'s which are <1 µM, <750 nM, <500 nM, <400 nM, <300 nM, <200 nM, <100 nM, <50 nM, <10 nM, <1 nM, <100 pM, <10 pM, <5 pM, <2 pM, or <1 pM when binding to the receptor complex CLR:RAMP1, CLR:RAMP2, and/or CLR:RAMP3 is measured.

The AM and CGRP variant peptides of the present disclosure have, but are not limited to, one of at least two effects: (1) an agonistic effect on the corresponding CLR:RAMP1-3 receptor complex, and (2) an antagonistic effect against the corresponding CLR:RAMP1-3 receptor complex. These effects lead to particular utilities. For example, AM peptides having agonistic effects (e.g., peptides having both N-terminal and C-terminal binding portions) can be used therapeutically for treatment of, for example, heart failure, acute myocardial infarction, pulmonary hypertension, preeclampsia, sepsis, lymphedema, lymphangectasia, and fertility (e.g., implantation during in vitro fertilization), and other conditions discussed elsewhere herein. AM peptides having antagonistic effects (e.g., peptides having only a C-terminal binding portion) can be used therapeutically for treatment of, for example, cancers as described elsewhere herein. CGRP peptides having antagonistic effects (e.g., peptides having only a C-terminal binding portion) can be used therapeutically for treatment of, for example, cancers, migraine headaches, and other conditions described elsewhere herein.

In certain embodiments, the present disclosure includes a method of treating a subject for a condition regulated by a calcitonin receptor-like receptor-receptor activity-modifying protein (CLR:RAMP) receptor complex, comprising the step of administering to a subject in need of such therapy, an effective amount of a variant peptide of at least one of adrenomedullin (AM), calcitonin gene-related peptide alpha (αCGRP), and calcitonin gene-related peptide beta (βCGRP). The CLR:RAMP receptor complex is one or more of CLR:RAMP1, CLR:RAMP2, and CLR:RAMP3.

An effective amount of a variant peptide composition of the present disclosure will generally contain sufficient active substance to deliver from about 0.01 µg/kg to about 100 mg/kg (weight of active substance/body weight of the subject). Particularly, the composition will deliver about 0.1 µg/kg to about 50 mg/kg, and more particularly about 1 µg/kg to about 20 mg/kg.

Practice of the methods of the present disclosure may comprise administering to a subject an effective amount of the variant peptide in any suitable systemic and/or local formulation in an amount effective to deliver the dosages listed above. The dosage can be administered, for example but not by way of limitation, on a one-time basis, or administered at multiple times (for example but not by way of limitation, from one to five times per day, or once or twice per week), or continuously via a venous drip, depending on the desired therapeutic effect. In one non-limiting example of a therapeutic method of the present disclosure, the variant peptide compound is provided in an IV infusion in the range of from about 0.01 mg/kg to about 10 mg/kg of body weight once a day.

Administration of the peptide compound used in the pharmaceutical composition or to practice the method of the present disclosure can be carried out in a variety of conventional ways, such as, but not limited to, orally, by inhalation, rectally, topically, nasally, or by cutaneous, subcutaneous, intraperitoneal, vaginal, or intravenous injection. Oral formulations may be formulated such that the variant peptide passes through a portion of the digestive system before being released, for example it may not be released until reaching the small intestine, or the colon.

When an effective amount of the variant peptide is administered orally, it may be in the form of a solid or a liquid preparation such as (but not limited to) capsules, pills, tablets, lozenges, melts, powders, suspensions, solutions, elixirs, or emulsions. Solid unit dosage forms can be capsules of the ordinary gelatin type containing, for example, surfactants, lubricants, and inert fillers such as lactose, sucrose, and cornstarch, or the dosage forms can be sustained release preparations. The pharmaceutical composition may contain a solid carrier, such as a gelatin or an adjuvant. The tablet, capsule, and powder may contain from about 0.05% to about 95% of the active substance compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol, or polyethylene glycol. When administered in liquid form, the pharmaceutical composition particularly contains from about 0.005% to about 95% by weight of the active substance. For example, a dose of about 10 mg to about 1000 mg once or twice a day could be administered orally.

In another embodiment, the variant peptides of the present disclosure can be tableted with conventional tablet bases such as (but not limited to) lactose, sucrose, and cornstarch in combination with binders, such as (but not limited to) acacia, cornstarch, or gelatin, disintegrating agents such as (but not limited to) potato starch or alginic acid, and a lubricant such as (but not limited to) stearic acid or magnesium stearate. Liquid preparations are prepared by dissolving the peptide compound in an aqueous or non-aqueous pharmaceutically acceptable solvent which may also contain suspending agents, sweetening agents, flavoring agents, and preservative agents as are known in the art.

For parenteral administration, for example, the peptide compounds may be dissolved in a physiologically acceptable pharmaceutical carrier and administered as either a solution or a suspension. Illustrative of suitable non-limiting pharmaceutical carriers are water, saline, dextrose solutions, fructose solutions, ethanol, or oils of animal, vegetative, or synthetic origin. The pharmaceutical carrier may also contain preservatives and buffers as are known in the art.

When an effective amount of the variant peptide is administered by intravenous, cutaneous, or subcutaneous injection, the compound is particularly in the form of a pyrogen-free, parenterally acceptable aqueous solution or suspension. The preparation of such parenterally acceptable solutions, having due regard to pH, isotonicity, stability, and the like, is well within the skill in the art. A particular pharmaceutical composition for intravenous, cutaneous, or subcutaneous injection may contain, in addition to the peptide compound, an isotonic vehicle such as (but not limited to) Sodium Chloride Injection, Ringer's Injection, Dextrose Injection, Dextrose and Sodium Chloride Injection, Lactated Ringer's Injection, or other vehicle as known in the art. The pharmaceutical compositions of the present disclosure may also contain stabilizers, preservatives, buffers, antioxidants, or other additives known to those of skill in the art.

As noted, particular amounts and modes of administration can be determined by one skilled in the art. One skilled in the art of preparing formulations can readily select the proper form and mode of administration, depending upon the particular characteristics of the peptide compound selected, the condition to be treated, the stage of the condition, and other relevant circumstances using formulation technology known in the art, described, for example, in *Remington: The Science and Practice of Pharmacy*, $21^{st}$ ed.

Additional pharmaceutical methods may be employed to control the duration of action of the variant peptide. Increased half-life and/or controlled release preparations may be achieved through the use of proteins or polymers to conjugate, complex with, and/or absorb the peptide as discussed previously herein. The controlled delivery and/or increased half-life may be achieved by selecting appropriate macromolecules (for example but not by way of limitation, polysaccharides, polyesters, polyamino acids, homopolymers, polyvinyl pyrrolidone, ethylenevinylacetate, methylcellulose, or carboxymethylcellulose, and acrylamides such as N-(2-hydroxypropyl) methacrylamide), and the appropriate concentration of macromolecules as well as the methods of incorporation, in order to control release.

Another possible method useful in controlling the duration of action of the peptide compound by controlled release preparations and half-life is incorporation of the peptide compound or its functional derivatives into particles of a polymeric material such as (but not limited to) polyesters, polyamides, polyamino acids, hydrogels, poly(lactic acid), ethylene vinylacetate copolymers, copolymer micelles of, for example, polyethylene glycol (PEG) and poly(1-aspartamide).

It is also possible to entrap the peptide compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are well known to persons having ordinary skill in the art.

When the variant peptide or peptide compound is to be used as an injectable material, it can be formulated into a conventional injectable carrier. Suitable carriers include (but not limited to) biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the US Food and Drug Administration, which are available to those in the field. The pharmaceutical composition may also be in the form of an aqueous solution containing many of the same substances as described above for the reconstitution of a lyophilized product.

The variant peptides can also be administered as a pharmaceutically acceptable acid- or base-addition salt, formed by reaction with inorganic acids such as (but not limited to) hydrochloric acid, hydrobromic acid, perchloric acid, nitric acid, thiocyanic acid, sulfuric acid, and phosphoric acid, and organic acids such as (but not limited to) formic acid, acetic acid, propionic acid, glycolic acid, lactic acid, pyruvic acid, oxalic acid, malonic acid, succinic acid, maleic acid, and fumaric acid, or by reaction with an inorganic base such as (but not limited to) sodium hydroxide, ammonium hydroxide, potassium hydroxide, and organic bases such as (but not limited to) mono-, di-, trialkyl and aryl amines, and substituted ethanolamines.

In certain embodiments, the present disclosure includes a variant peptide composition including: at least one variant peptide coupled directly or indirectly to a carrier molecule, wherein the at least one variant peptide is from 10 to 70 amino acids in length.

The compounds, conjugates, compositions, and methods of production and application of the variant peptides described herein can be made and executed without undue experimentation in light of the present disclosure. While the present disclosure has been described in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the presently disclosed methods and compositions. Changes may be made in the formulation of the various compositions described herein, the methods described herein or in the steps or the sequence of steps of the methods described herein without departing from the spirit and scope of the present disclosure.

What is claimed is:

1. A variant peptide having binding affinity for at least one receptor complex of the group consisting of calcitonin receptor-like receptor-receptor activity-modifying protein 1 (CLR:RAMP1), calcitonin receptor-like receptor-receptor activity-modifying protein 2 (CLR:RAMP2), and calcitonin receptor-like receptor-receptor activity-modifying protein 3 (CLR:RAMP3), the variant peptide having an affinity $K_i$ for the receptor complex of less than 1 µM, and the variant peptide having a structure as represented by Formula I (SEQ ID NO:49):

$$X_1\text{-}K\text{-}X_3\text{-}N\text{-}V\text{-}A\text{-}P\text{-}R\text{-}X_9\text{-}X_{10}\text{-}X_{11}\text{-}X_{12}\text{-}P\text{-}X_{14}\text{-}G\text{-}X_{16} \quad (I)$$

wherein:
$X_1$ is A, D, V, L, or I,
$X_3$ is D, F, M, Y, V, I, E, K, W, L, or R,
$X_9$ is S, W, Y, F, R, T, or L,
$X_{10}$ is K, G, L, M, Y, A, W, or F,
$X_{11}$ is I, L, or M,
$X_{12}$ is S, T, or G,
$X_{14}$ is Q, F, Y, W, or H, and
$X_{16}$ is Y or F, wherein the Y or F is amidated;
with the proviso that the variant peptide comprises at least one substitution selected from the group consisting of:
$X_1$ is A, V, L, or I;
$X_3$ is F, M, Y, V, I, K, W, L, or R;
$X_9$ is W, Y, F, R, or L;
$X_{10}$ is G, L, M, Y, A, W, or F; and
$X_{14}$ is F, Y, W, or H; and
wherein the variant peptide is optionally extended at the N-terminus by all or any portion of amino acids 1-36 of SEQ ID NO:1, by all or any portion of amino acids 1-22 of SEQ ID NO:31, by all or any portion of amino acids 1-22 of SEQ ID NO:32, or by all or any portion of amino acids 1-24 of SEQ ID NO:47.

2. The variant peptide of claim 1, wherein the variant peptide is bound to a carrier molecule, and optionally is bound to the carrier molecule by a linker molecule.

3. The variant peptide of claim 1, further defined as consisting of up to 70 amino acids.

4. The variant peptide of claim 1, further defined as having agonistic activity for the at least one receptor complex.

5. The variant peptide of claim 1, further defined as having antagonistic activity for the at least one receptor complex.

6. The variant peptide of claim 1, wherein the affinity $K_i$ is less than about 500 nM.

7. A method of treating a subject for a condition regulated by a calcitonin receptor-like receptor-receptor activity-modifying protein (CLR:RAMP) receptor complex, comprising the step of:
administering to a subject in need of such therapy an effective amount of a variant peptide having binding affinity for at least one receptor complex of the group consisting of calcitonin receptor-like receptor-receptor activity-modifying protein 1 (CLR:RAMP1), calcitonin receptor-like receptor-receptor activity-modifying protein 2 (CLR:RAMP2), and calcitonin receptor-like receptor-receptor activity-modifying protein 3 (CLR:RAMP3), the variant peptide having an affinity $K_i$ for the receptor complex of less than 1 µM, and the variant peptide having a structure as represented by Formula I (SEQ ID NO:49):

$$X_1\text{-}K\text{-}X_3\text{-}N\text{-}V\text{-}A\text{-}P\text{-}R\text{-}X_9\text{-}X_{10}\text{-}X_{11}\text{-}X_{12}\text{-}P\text{-}X_{14}\text{-}G\text{-}X_{16} \quad (I)$$

wherein:
$X_1$ is A, D, V, L, or I;
$X_3$ is D, F, M, Y, V, I, E, K, W, L, or R;
$X_9$ is S, W, Y, F, R, T, or L;
$X_{10}$ is K, G, L, M, Y, A, W, or F;
$X_{11}$ is I, L, or M;
$X_{12}$ is S, T, or G;
$X_{14}$ is Q, F, Y, W, or H; and
$X_{16}$ is Y or F, wherein the Y or F is amidated;
with the proviso that the variant peptide comprises at least one substitution selected from the group consisting of:
$X_1$ is A, V, L, or I;
$X_3$ is F, M, Y, V, I, K, W, L, or R;

$X_9$ is W, Y, F, R, or L;
$X_{10}$ is G, L, M, Y, A, W, or F; and
$X_{14}$ is F, Y, W, or H; and wherein the variant peptide is optionally extended at the N-terminus by all or any portion of amino acids 1-36 of SEQ ID NO:1, by all or any portion of amino acids 1-22 of SEQ ID NO:31, by all or any portion of amino acids 1-22 of SEQ ID NO:32, or by all or any portion of amino acids 1-24 of SEQ ID NO:47.

8. The method of claim 7, wherein the CLR:RAMP receptor complex is CLR:RAMP1.

9. The method of claim 7, wherein the CLR:RAMP receptor complex is CLR:RAMP2.

10. The method of claim 7, wherein the CLR:RAMP receptor complex is CLR:RAMP3.

11. The variant peptide of claim 1, wherein $X_{14}$ is F, Y, or W.

12. The variant peptide of claim 1, wherein $X_9$ is W and $X_{14}$ is F, Y, or W.

13. The variant peptide of claim 1, wherein $X_{12}$ is G and $X_{14}$ is F, Y, or W.

14. The method of claim 7, wherein in the variant peptide, $X_{14}$ is F, Y, or W.

15. The method of claim 7, wherein in the variant peptide, $X_9$ is W and $X_{14}$ is F, Y, or W.

16. The method of claim 7, wherein in the variant peptide, $X_{12}$ is G and $X_{14}$ is F, Y, or W.

17. A variant peptide having binding affinity for at least one receptor complex of the group consisting of calcitonin receptor-like receptor-receptor activity-modifying protein 1 (CLR:RAMP1), calcitonin receptor-like receptor-receptor activity-modifying protein 2 (CLR:RAMP2), and calcitonin receptor-like receptor-receptor activity-modifying protein 3 (CLR:RAMP3), the variant peptide having an affinity $K_i$ for the receptor complex of less than 1 μM, and the variant peptide having a structure as represented by Formula I (SEQ ID NO:49):

X1-K-X3-N-V-A-P-R-X9-X10-X11-X12-P-X14-G-X16  (I)

wherein:
$X_1$ is A, D, V, L, or I;
$X_3$ is F, I, Y, V, I, E, K, V, L, or R;
$X_9$ is S, W, Y, F, R, T, or L;
$X_{10}$ is K, G, M, Y, A, W, or F;
$X_{11}$ is I, L, or M;
$X_{12}$ is S, T, or G;
$X_{14}$ is Q, F, Y, W, or H; and
$X_{16}$ is Y or F, wherein the Y or F is amidated;

with the proviso that the variant peptide does not include amino acids 37-52 of SEQ ID NO: 1 in a contiguous sequence; and wherein the variant peptide is extended at the N-terminus by all or a fragment of at least 4 contiguous amino acids 1-22 of SEQ ID NO:31, by all or a fragment of at least 4 contiguous amino acids 1-22 of SEQ ID NO:32, or by all or a fragment of at least 5 contiguous amino acids 1-24 of SEQ ID NO:47.

18. The variant peptide of claim 17, wherein $X_{14}$ is F, Y, or W.

19. The variant peptide of claim 17, wherein $X_9$ is W and $X_{14}$ is F, Y, or W.

20. The variant peptide of claim 17, wherein $X_{12}$ is G and $X_{14}$ is F, Y, or W.

21. The variant peptide of claim 17, wherein the variant peptide is bound to a carrier molecule, and optionally is bound to the carrier molecule by a linker molecule.

22. The variant peptide of claim 17, further defined as consisting of up to 70 amino acids.

23. The variant peptide of claim 17, further defined as having agonistic activity for the at least one receptor complex.

24. The variant peptide of claim 17, further defined as having antagonistic activity for the at least one receptor complex.

25. The variant peptide of claim 17, wherein the affinity $K_i$ is less than about 500 nM.

* * * * *

UNITED STATES PATENT AND TRADEMARK OFFICE
CERTIFICATE OF CORRECTION

PATENT NO. : 10,464,983 B2
APPLICATION NO. : 15/568129
DATED : November 5, 2019
INVENTOR(S) : Augen A. Pioszak It is certified that error appears in the above-identified patent and that said Letters Patent is hereby corrected as shown below:

In the Specification

Column 21, Line 7: Delete "REFMACS" and replace with -- REFMAC5 --

Column 21, Line 43: Delete "REFMACS" and replace with -- REFMAC5 --

Column 21, Line 51: Delete "REFMACS" and replace with -- REFMAC5 --

Column 21, Line 57: Delete "Ca" and replace with -- Cα --

Column 29, Line 24: After "CLR" delete "al" and replace with -- α1 --

Column 30, Line 29: Delete "RAMPS:" and replace with -- RAMPs: --

Column 31, Line 56: Delete "147," and replace with -- I47, --

Signed and Sealed this
Tenth Day of December, 2019

Andrei Iancu
*Director of the United States Patent and Trademark Office*